United States Patent
Hirose et al.

(12)

(10) Patent No.: US 6,565,858 B2
(45) Date of Patent: *May 20, 2003

(54) HUMAN ADAMTS-1 PROTEIN AND PHARMACEUTICAL COMPOSITION

(75) Inventors: Kunitaka Hirose, Tokyo (JP); Eiji Inoguchi, Gunma (JP); Michinori Hakozaki, Fukushima (JP); Keiko Ishioka, Tokyo (JP); Yukako Ishida, Tokyo (JP); Kouji Matsushima, Chiba (JP); Kouji Kuno, Ishikawa (JP)

(73) Assignee: Kureha Chemical Industry Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/445,023

(22) PCT Filed: Jun. 3, 1998

(86) PCT No.: PCT/JP98/02449

§ 371 (c)(1),
(2), (4) Date: Dec. 3, 1999

(87) PCT Pub. No.: WO98/55643

PCT Pub. Date: Dec. 10, 1998

(65) Prior Publication Data

US 2002/0119167 A1 Aug. 29, 2002

(30) Foreign Application Priority Data

Jun. 3, 1997 (JP) .............................. 9-160422

(51) Int. Cl.[7] .......................... A61K 45/00; A61K 47/00
(52) U.S. Cl. ..................... 424/278.1; 530/350; 530/400
(58) Field of Search ....................... 424/278.1; 530/350, 530/400

(56) References Cited

FOREIGN PATENT DOCUMENTS

| EP | 0 874 050 A2 | 10/1998 |
|---|---|---|
| WO | WO 99/07850 | 2/1999 |

OTHER PUBLICATIONS

Colige et al. J. Biol. Chem 270: 16724–16730, 1995.*
Shinclo et al. J. Clin. Invest. 105: 1345–1352, 2000.*
Kuno et al. J. Biol. Chem. 272(1): 556–562, 1997.*
Vazquez et al., *Meth–1, a Human Ortholog of ADAMTS–1, and Meth–2 Are Members of a New Family of Proteins with Angio–inhibitory Activity*, J. Biol. Chem. 274(33):23349–23357 (1999).
Vazquez et al., *Meth–1 and Meth–2 are novel proteins that contain the anti–angiogenic domain of thrombospondin*, Faseb J. 11(3):A336 (1997) Abstract.
European Search Report Nov. 27, 1961.
Colige et al., *Proc. Natl. Acad. Sci. USA* 94:2374–2379 (1997).

* cited by examiner

Primary Examiner—Patrick J. Nolan
Assistant Examiner—Gerald R. Ewoldt
(74) Attorney, Agent, or Firm—Sughrue Mion, PLLC

(57) ABSTRACT

A human ADAMTS-1 protein, a gene encoding the same, a pharmaceutical composition containing the protein as an active ingredient, and a method for immunologically analyzing the human ADAMTS-1 protein are disclosed. The protein can decrease the number of leukocytes and platelets, and at the same time, increase the number of erythrocytes.

7 Claims, 17 Drawing Sheets

FIG. 2

```
Mouse ADAMTS-1  2101' ACTGCTCAAGAACCTGTGGTGGTGGAGTTCAATACACAATGAGAGAATGTGACAACCCAG
                       ::::::::::::::::::::::::::::::::  :::  :::  ::  :::::::::
Frag.1             1'      CAAGAACCTGTGTGGTGGAGTTCATTACACGATGAGGGATTGTTACAACCCAG 2161' TCCCAAAGAACGGAGGGAAGTACTGTGAAGGCAAACGAGTCCGCTACAGGTCCTGTAACA
                       :::::::::  ::  :::  ::   :::::::::: ::  :::::::::::  ::
                  55'  TCCCAAAGATTGGAGGGAAGTCTTGTAAAGGCAAACGAGTGCCCTACAGTTCCTTTATCC 2221' TCGAGGACTGTCCAGACAATAACGGAAAAACG--TTCAGAGAGGAGCAGTGCGAGGCG-C
                       ::  ::: ::::::  ::  ::  :: :::   :::::: ::  :::::::: :
                 115' TTTAGGACTGTCTAGACAATTACTGGAATTCGACTTAAGAGTGGCCCA-TCCTATGCGCC 2278' ACAATGAGTTTCCAAAGCTTCCTTTGGGAATGAGCCCACTGTAG-AGTGG-ACACCCAA
                       ::  :  ::::::::: :::::::::::::  :: : ::::   :  ::::::::::
                 174' ACACCGCGTTTCAAAATGTTTCCTTTGGGAGTTGGGCTGCGGGTGGAATTGGTTTCCCAA 2336' GTACGCCGGCGTCTCGCCAAAGGACAGGTGCAAGCTCA-CCTGTGAAGCCAAAGGCATTG
                       :::  ::::::::::::::: ::::::::::::::::::: ::::::::::::: :::
                 234' GGATCGTGGCGTCTCACCAAAGGACAGGTGCAAGCTCATCATGCCAAGCCAAAGG-ATTG 2395' GCTACTTTTCGTCTTACAGCCCAAGGTTGTAGATGGCACTCCCTGTAGTCCAGACTCTA
                       ::::: :::::  :::::
                 293' GCTACATTTTC
```

FIG. 5

| | | |
|---|---|---|
| Hu ADAMTS-1 | 1' | ATGGATATCTGCAGAATTCGGCTTAGGAAGAAGCGATTTGTGTCCAGCCCCGTTATGTG |
| Mu ADAMTS-1 | 1" | **  *  *  ****************  *  ******************************** |
| | 61' | AAGCCATCAGGACCAGGAAGCATAAGGAAGAAGCGATTTGTGTCCAGCCCCGTTATGTG |
| | 61" | GAAACCATGCTTGTGGCAGACCAGTCGATGGCAGAATTCCACGGCAGTGGTCTAAAGCAT |
| | 121' | GAAACCATGCTCGTCGTAGCTGTGACCAGTCCATGGCCGACTTCCACGGCAGCGGTCTAAAGCAT |
| | 121" | TACCTTTCTCACGTTTGTTTTCGGTGGCAGCCAGATTGTACAAACACCCCAGCATTCGTAAT |
| | 181' | TACCTTCTAACCCTGTTCTCGGTGCCAGCCAGGTTTTACAAGCATCCCAGCATTAGGAAT |
| | 181" | TCAGTTAGCCTGGTGGTGGTGAAGATCTTGGTCATCCACGATGAACAGAAGGGGCCGGAA |
| | 241' | TCAATTAGCCTGGTGGTGGTGGTGAAGATCTTGGTCATATACGAGGAGCAGAAGGGACCAGAA |
| | 241" | GTGACCTCCAATGCTGCCCCTCACTCTGCGGAACTTTTGCAACTGGCAGAAGCAGCACAAC |
| | 301' | GTTACCTCCAATGCAGCTGGGATCCAGAGCACTATGACACAGCAATTCTTTTCACCAGACAGGAC |
| | 301" | CCACCCAGTGACCGGATGCAGAGCACTATGACACAGCAATTCTTTTCACCAGACAGGAC |
| | 361' | AGCCCCAGTGACCGGGATCCAGAGCACTATGACACTGCAATTCTGTTCACCAGACAGGAT |
| | 361" | TTGTGTGGGTCCCAGACATGTGATACTCTTGGGATGGCTGATGTTGGAACTGTGTGTGAT |
| | 421' | TTATGTGGCTCCCACACGTGTGACACTCTCGGAATGGCAGATGTTGGAACCGTATGTGAC |
| | 421" | CCGAGCAGAAGCTGCTCCGTCATAGAAGATGATGGTTTACAAGCTGCCTTCACCACAGCC |
| | | CCCAGCAGGAGCTGCTCAGTCATAGAAGATGATGGTTTGCAAGCTGCCTTCACCACAGCC |

FIG. 6

```
Hu ADAMTS-1  481'  CATGAATTAGGCCACGTGTTTAACATGCCACATGATGATGCAAAGCAGTGTGCCAGCCTT
Mu ADAMTS-1  481"  CATGAATTGGGCCATGTGTTTAACATGCCGCACGATGATGCTAAGCACTGTGCCAGCTTG

541'  AATGGTGTGAACCAGGATTCCCACATGATGGCGTCAATGCTTTCCAACCTGGACCACAGC
             541"  AATGGTGTGAGTGGCGGCGATTCTCATCTGATGCCCTCGATGCTCTCCAGCTTAGACCATAGC

601'  CAGCCTTTGGTCTCTCCTTGCAGTGCCTACATGATTACATCATTTCTGGATAATGGTCATGGG
             601"  CAGCCCTGGTCACCTTGCAGTGCCTACATGGTCACGTCCTTCCTAGATAATGGACACGGG

661'  GAATGTTTGATGGACAAGCCTCAGAATCCCATACACAGCTCCCAGGCGATCTCCCTGGCACC
             661"  GAATGTTTTGATGGACAAGCCCCAGAATCCAATCAAGCTCCCTTCTGATCTTCCCGGTACC

721'  TTGTACGATGCCAACCGGCAGTGCCAGTTTACATTTGGGGAGGACTCCAAACACTGCCCC
             721"  TTGTACGATGCCAACCGCCAGTGTCAGTTTACATTCGGAGAGGAATCCAAGCACTGCCCT

781'  GATGCCAGCCAGCACATGTAGCCACCTTGTGGTGTACCGGCACCTCTGGTGGGGTGCTGGTG
             781"  GATGCCAGCCAGCACATGTACTACCCTGTGGTGCACTGGCACCTCCGGTGGCTTACTGGTG

841'  TGTCAAACCAAACACTTCCCCGTGGGCGGATGGCACCAGCTGTGGAGAAGGGAAATGGTGT
             841"  TGCCAAACAAAACACTTCCCTTGGGCAGATGGCACCAGCTGTGTGGAGAAGGGAAGTGGTGT

901'  ATCAACGGCAAGTGTGTGAACAAAACCGACAGGAAGCATTTTGATACGCCTTTTCATGGA
             901"  GTCAGTGGCAAGTGCGTGAACAAGACAGACATGAAGACATTTTGCTACTCCTGTTCATGGA
```

FIG. 7

```
Hu ADAMTS-1   961'  AGCTGGGACCATGGGGACCGTGGGGAGGAGACTGTTCGAGAACGTGCGGTGGAGGAGTCCAG
Mu ADAMTS-1   961"  AGCTGGGACCATGGGGACCGTGGGGAGGAGACTGCTCAAGAACCTGTGGTGGAGTTCAA

1021'  TACACGATGAGGGAATGTGACAACCCAGTCCCAAAGAATGGAGGAAGTACTGTGAAGGC
             1021"  TACACAATGAGAGAGAATGTGACAACCCAGTCCCAAAGAACGGAGGAAGTACTGTGAAGGC

1081'  AAACGAGTGCGCTACAGATCCTGTAACCTTGAGGACTGTCCAGACAATAATGGAAAAACC
             1081"  AAACGAGTCCGCTACAGGTCCTGTAACATCGAGGACTGTCCAGACAATAACGGAAAAACG

1141'  TTTAGAGAGGAACAATGTGAAGCACACAACGAGTTTTCAAAAAGCTTCCTTTGGGAGTGGG
             1141"  TTCAGAGAGGAGCAGTGCGAGGCGCACAATGAGTTTTCCAAAAGCTTCCTTTGGGAATGAG

1201'  CCTGCGGTGGAATGGATTCCCAAGTACGCTGGCGTCTCACCAAAGGACAGGTGCAAGCTC
             1201"  CCCACTGTAGAGTGGACACCCAAGTACGCCGGCGTCTCGCCAAAGGACAGGTGCAAGCTC

1261'  ATCTGCCAAGCCAAAGGCATTGGCTACTTCTTCGTTTTGCAGCCCAAGGTTGTTGATGGT
             1261"  ACCTGTGAAGCCAAAGGCATTGGCTACTTTTCGTCTTACAGCCCAAGGTTGTAGATGGC

1321'  ACTCCATGTAGCCCAGATTCCACCTCTGTGTCTGTGCAAGGACAGTGTGTAAAAGCTGGT
             1321"  ACTCCCTGTAGTCCAGACTCTACCTCTGTGTCTGTGCAAGGGCAGTGTGTGAAAGCTGGC

1381'  TGTGATCGCATCATAGACTCCAAAAAGAAGTTTGATAAATGTGGTGTTTGCGGGGAAAT
             1381"  TGTGATCGCATCATAGACTCCAAAAAGAAGTTTGATAAGTGTGGCGTTTGTGGAGGAAAC
```

FIG. 8

```
Hu ADAMTS-1 1441' GGATCTACTTGTAAAAAATATCAGGATCAGTTACTAGTGCAAAACCTGGATATCATGAT
                  *** ****  *** *  *** ****    ****   *** ****************
Mu ADAMTS-1 1441" GGTTCCACATGCAAGAAGATGTCAGGAATAGTCACTAGTACAAGACCTGGGTATCATGAC

1501' ATCGTCACAATTCCAACTGGAGCCACCAACATCGAAGTGAAACAGCGGAACCAGAGGGGA
                  ** ****** *** **** ***   ***  * *************
            1501" ATTGTCACAATTCCTGCTGGAGCCACCAACATTGAAGTGAAACATCGGAATCAAAGGGGG

1561' TCCAGGAACAATGGCAGCTTTCTTGCCATCAAAGCTGCTGATGGCACATATATTCTTAAT
                  ********* ******** ****** *** ******** ************ *** *
            1561" TCCAGAAACAATGGCAGCTTTCTCTGGCTTATTAGAGCCGCTGATGGTACCTATATTCTGAAT

1621' GGTGACTACACTTTGTCCACCTTAGAGCAAGACATTATGTACAAAGGTGTTGTCTTGAGG
                  ** *  ***  ***  *  ****   *  *     *                  ****
            1621" GGAAACTTCACTCTGTCCACACTAGAGCAAGACCTCACCTACAAAGGTACTGTCTTAAGG

1681' TACAGCGGCTCCTCCTCTGCGGCATTGGAAAGAATTCGCAGCTTTAGCCCCTCTCAAAGAGCCC
                  *******  ****** ** ***** *************  ******** ***  ****
            1681" TACAGTGGTTCCTCGGCTGCGCGCTGGAAAAGAATCCGCAGCTTTAGTCCACTCAAAGAACCC

1741' TTGACCATCCAGGTTCTTACTGTGGGCAATGCCCCTTCGACCTAAAATTAAATACACCTAC
                  ** ***********  **    **  *   **** ********  ****  ******
            1741" TTAACCATCCAGGTTCTTTATGGTAGGCCATGCCATGCTCTCCGACCCAAAATTAAATTCACCTAC

1801' TTCGTAAAAGAAGAAGAAGGAATCTTTCAATGCTTTCAGCATGGGTCATT
                  *                  ***                     ****  ******   ****
            1801" TTTATGAAGAAGAAGACAGAGTCATTCAACGCCATTCCCACATTTCTGAGTGGGTGATT

1861' GAAGAGTGGGGCGAATGTTCTAAGTCATGTGAATTGGGTTGGCAGAGAAGACTGGTAGAA
                  ************                       ***              *  **
            1861" GAAGAGTGGGGGGAGTGCTCCAAGACATGCGGCTCAGGTTCCAGGTTGGCAGAGAAGAGTAGTGCAG
```

FIG. 9

```
Hu ADAMTS-1 1921'  TGCCGAGACATTAATGGACACAGCCTGCTTCCGAGTGTGCAAAGGAAGTGAAGCCAGCCAGC
                  *** ******************** **** ****************************** ***
Mu ADAMTS-1 1921" TGCAGAGACATTAACGGACACACCCCTGCTTCCGAATGTGCAAAGTGAAGCCAGCCAGT

1981' ACCAGACCTTGTGCAGACCATCCCTGCCCCCCAGTGGCAGCTGGGGGAGTGGTCATCATGT
                   *** ***************** **** ****************** **** ****** ****
             1981" ACCAGACCCTTGTGCAGACCTTCCTTGCCCACACTGGCCAGGTGGGGGATTGGTCACCATGT

2041' TCTAAGACCTGTGGGGAAGGGTTACAAAAAAAGAAGCTTGAAGTGTCTCTGTCCCATGATGGA
                   *** *** ******************* ********** ********* ** ********* ****
             2041" TCCAAAACTTGCGGGAAGGGTTACAAGAAGAGAACCTTGAAATGTGTCCCACGATGGG

2101' GGGGTGTTATCTCATGAGAGCTGTGTGATCCTTTAAAGAAACCTAAACATTTCATAGACTTT
                   *** ***** ******** ******************* ** ****** *********** ****
             2101" GGCCTGTTATCAAATGAGAGCTGTGATCCTTTGAAGAAGCCAAAGCATTACATTGACTTT

2161' TGCACACTGACACAGTGCAGTTAA
                   *** ***********************
             2161" TGCACACTGACACAGTGCAGTTAA
```

FIG. 10

```
                           ┌→MMP domain
Hu ADAMTS-1   1'   MDICRIRLRKK|RFVSSPRYVETMLVADQSM
                         * * *|* * * * * * * * * * * * * * * * * * *
Mu ADAMTS-1   1"   EPSGPGSIRKK|RFVSSPRYVETMLVADQSM 31'    AEFHGSGLKHYLLTLFSVAARLYKHPSIRN
                   *  * * * * * * * * * * * * * * * * * *  * * * * * * *
            31"    ADFHGSGLKHYLLTLFSVAARFYKHPSIRN 61'    SVSLVVVKILVIHDEQKGPEVTSNAALTLR
                   *  * * * * * * * * *    * * * * * * * * * * * * * * *
            61"    SISLVVVKILVIYEEQKGPEVTSNAALTLR 91'    NFCNWQKQHNPPSDRDAEHYDTAILFTRQD
                   * * *  * * * * * *  * * * * *  * * * * * * * * * * *
            91"    NFCSWQKQHNSPSDRDPEHYDTAILFTRQD 121'   LCGSQTCDTLGMADVGTVCDPSRSCSVIED
                   * * * *  * * * * * * * * * * * * * * * * * * * * * *
            121"   LCGSHTCDTLGMADVGTVCDPSRSCSVIED
                             [zinc binding
                                 site]
            151'   DGLQAAFTTAHELGHVFNMPHDDAKQCASL
                   * * * * * * * * * * * * * * * * * * * * * * *  * * * *
            151"   DGLQAAFTTAHELGHVFNMPHDDAKHCASL 181'   NGVNQDSHMMASMLSNLDHSQPWSPCSAYM
                   * * *    * * *   * * * * * *  * * * * * * * * * * * *
            181"   NGVSGDSHLMASMLSSLDHSQPWSPCSAYM ┌→DI domain
            211'   ITSFLDNGHGECLMDKPQNPIQLP|GDLPGT
                    * * * * * * * * * * * * * * * * * * * *  * *|* * * * *
            211"   VTSFLDNGHGECLMDKPQNPIKLP|SDLPGT
```

FIG. 11

```
Hu ADAMTS-1  241'  L Y D A N R Q C Q F T F G E D S K H C P D A A S T C S T L W
                   * * * * * * * * * * * * *   * * * * * * * * * * *   * * *
Mu ADAMTS-1  241"  L Y D A N R Q C Q F T F G E E S K H C P D A A S T C T T L W

271'  C T G T S G G V L V C Q T K H F P W A D G T S C G E G K W C
                   * * * * * * *   * * * * * * * * * * * * * * * * * * * * *
             271"  C T G T S G G L L V C Q T K H F P W A D G T S C G E G K W C

TSP domain
             301'  I N G K C V N K T D R K H F D T P F H G S W G P W G P W G D
                   * * * * * * * *   * * *   * *   * * * * * * * * * * * *
             301"  V S G K C V N K T D M K H F A T P V H G S W G P W G P W G D 331'  C S R T C G G G V Q Y T M R E C D N P V P K N G G K Y C E G
                   * * * * * * * * * * * * * * * * * * * * * * * * * * * * *
             331"  C S R T C G G G V Q Y T M R E C D N P V P K N G G K Y C E G 361'  K R V R Y R S C N L E D C P D N N G K T F R E E Q C E A H N
                   * * * * * * * * *   * * * * * * * * * * * * * * * * * * *
             361"  K R V R Y R S C N I E D C P D N N G K T F R E E Q C E A H N 391'  E F S K A S F G S G P A V E W I P K Y A G V S P K D R C K L
                   * * * * * * * *     *     * * *   * * * * * * * * * * * *
             391"  E F S K A S F G N E P T V E W T P K Y A G V S P K D R C K L 421'  I C Q A K G I G Y F F V L Q P K V V D G T P C S P D S T S V
                     *   * * * * * * * * * * * * * * * * * * * * * * * * * *
             421"  T C E A K G I G Y F F V L Q P K V V D G T P C S P D S T S V 451'  C V Q G Q C V K A G C D R I I D S K K K F D K C G V C G G N
                   * * * * * * * * * * * * * * * * * * * * * * * * * * * * *
             451"  C V Q G Q C V K A G C D R I I D S K K K F D K C G V C G G N 481'  G S T C K K I S G S V T S A K P G Y H D I V T I P T G A T N
                   * * * * * *   * *   * * *   * * * * * * * * *   * * *
             481"  G S T C K K M S G I V T S T R P G Y H D I V T I P A G A T N
```

FIG. 12

```
Hu  ADAMTS-1  511'  IEVKQRNQRGSRNNGSFLAIKAADGTYILN
                    ****  ******************  *********
Mu  ADAMTS-1  511"  IEVKHRNQRGSRNNGSFLAIRAADGTYILN

541'  GDYTLSTLEQDIMYKGVVLRYSGSSAALER
                    *  ********   ***  ************
              541"  GNFTLSTLEQDLTYKGTVLRYSGSSAALER

571'  IRSFSPLKEPLTIQVLTVGNALRPKIKYTY
                    *****************  ** *******  **
              571"  IRSFSPLKEPLTIQVLMVGHALRPKIKFTY
```

TSP domain
```
              601'  FVKKKKESFNAIPTFSA|WVIEEWGECSKSC
                    *  ***  **********  |***********  *
              601"  FMKKKTESFNAIPTFSE|WVIEEWGECSKTC 631'  ELGWQRRLVECRDINGQPASECAKEVKPAS
                    *****  *  ****  **********
              631"  GSGWQRRVVQCRDINGHPASECAKEVKPAS
```

TSP domain
```
              661'  TRPC|ADHPCPQ|WQLGEWSSCSKTCGKGYKK
                    ****|**  ***|**  *  **  ***********
              661"  TRPC|ADLPCPH|WQVGDWSPCSKTCGKGYKK 691'  RSLKCLSHDGGVLSHESCDPLKKPKHFIDF
                    *  *  ****  ********  *
              691"  RTLKCVSHDGGVLSNESCDPLKKPKHYIDF

721'  CTLTQCS
                    *******
              721"  CTLTQCS
```

HUMAN ADAMTS-1 PROTEIN AND PHARMACEUTICAL COMPOSITION

This application is a 371 national stage application of PCT/JP98/02449, filed Jun. 3, 1998, which claims the benefit of priority to Japan Application No. 9-160422, filed Jun. 3, 1997.

TECHNICAL FIELD

The present invention relates to a human ADAMTS-1 protein, a gene encoding the same, a pharmaceutical composition, and a method for immunologically analyzing the human ADAMTS-1 protein.

BACKGROUND ART

A mouse ADAMTS (A disintegrin and metalloproteinase with thrombospondin motifs)-1 gene has been cloned as a cDNA from a mouse colon cancer cell which induces cancer cachexia when transplanted to a mouse. The mouse ADAMTS-1 protein encoded by the gene is a unique protein containing a matrix metalloproteinase domain, a disintegrin domain, and three thrombospondin domains [J. Biol. Chem., 272, 556–562 (1997)]. The physiological functions of the mouse ADAMTS-1 protein has not been reported, but there have been reports of each individual functional domain contained therein.

For example, a snake venom disintegrin belongs to a family of proteins which are rich in cystein, and exhibit an anticoagulant activity [Semin. Hematol., 31, 289–300 (1994)].

Further, for example, an ADAM (A disintegrin and metalloproteinase) family is known as a protein family containing a matrix metalloproteinase domain and a disintegrin domain [Nature, 377, 652–656 (1995); Nature Genet., 5, 151–157 (1993); Nature, 356, 248–252 (1992)]. Examples of known ADAM family proteins are fertilin, epidermal apical protein, cyritestin, MDC (metalloprotease-like, disintegrin-like and cystein-rich protein), meltrin, MS2, and metargidin [Nature, 377, 652–656 (1995); Nature Genet. 5, 151–157 (1993); Nature, 356, 248–252 (1992); Biochem. J., 286, 671–675 (1992); Dev. Growth. Differ., 36, 49–58 (1994); Int. Immunol., 2, 585–591 (1990); J. Biol. Chem., 271, 4593–4596 (1996)].

It was reported that fertilin is involved in an integrin-mediated sperm-egg binding [Nature, 356, 248–252 (1992)], and meltrin is involved in a myotube formation [Nature, 377, 652–656 (1995)]. MDC expressed mainly in a central nervous system is a candidate as a suppresser against a human breast cancer [Nature Genet. 5, 151–157 (1993)], and MS2 serves as a macrophage antigen [Int. Immunol., 2, 585–591 (1990)]. However, little have been known about the physiological roles of these ADAM family proteins.

The mouse ADAMTS-1 protein contains a matrix metalloproteinase domain and a disintegrin domain, and therefore belongs to the ADAM family. However, the mouse ADAMTS-1 protein is different from other known ADAM family proteins in that it further contains thrombospondin domains.

As mentioned, the ADAM family proteins have various kinds of activities such as the involvement of bone or muscle metabolism, suppression of cancer growth, or fertilization, and the thrombospondin exhibits an action to inhibit vascularization and suppresses cancer. Therefore, it is expected that the mouse ADAMTS-1 protein will exhibit unique physiological functions.

The inventors of the present invention attempted to isolate the corresponding human ADAMTS-1 protein. Accordingly, the present inventors designed and prepared various probes on the basis of the base sequence of the known mouse ADAMTS-1 gene, and carried out plaque hybridizations with a human kidney cDNA library so as to obtain a human ADAMTS-1 gene, but a desired gene was not obtained. Then, the present inventors designed and prepared various primers on the basis of the base sequence of the known mouse ADAMTS-1 gene, and carried out PCRs, using the human kidney cDNA library as templates under ordinary conditions, so as to obtain the desired gene, but did not succeed.

Thereafter, the present inventors carried out a PCR of the human kidney cDNA library, using the same primers, but under conditions milder than those ordinarily used, more particularly, an annealing temperature is set lower than an ordinary temperature, and the inventors successfully obtained a novel human ADAMTS-1 gene. The resulting gene was then, expressed in *E. coli*, and the biological activities of the recombinant human ADAMTS-1 protein were examined. Surprisingly, it was found that the novel human ADAMTS-1 protein can decrease the numbers of leukocytes and platelets, and at the same time, increase the number of erythrocytes. Such activities in influencing hematopoietic functions cannot be expected from the structure of the mouse ADAMTS-1 gene which was used as the basis in designing the primers, or from the functions of domains contained in the human ADAMTS-1 protein. The present invention is based on the above findings.

DISCLOSURE OF INVENTION

The present invention relates to a protein characterized by containing an amino acid sequence of SEQ ID NO: 1:

Met Asp Ile Cys Arg Ile Arg Leu Arg Lys Lys Arg Phe Val Ser Ser

Pro Arg Tyr Val Glu Thr Met Leu Val Ala Asp Gln Ser Met Ala Glu

Phe His Gly Ser Gly Leu Lys His Tyr Leu Leu Thr Leu Phe Ser Val

Ala Ala Arg Leu Tyr Lys His Pro Ser Ile Arg Asn Ser Val Ser Leu

Val Val Val Lys Ile Leu Val Ile His Asp Glu Gln Lys Gly Pro Glu

Val Thr Ser Asn Ala Ala Leu Thr Leu Arg Asn Phe Cys Asn Trp Gln

Lys Gln His Asn Pro Pro Ser Asp Arg Asp Ala Glu His Tyr Asp Thr

-continued

Ala Ile Leu Phe Thr Arg Gln Asp Leu Cys Gly Ser Gln Thr Cys Asp
Thr Leu Gly Met Ala Asp Val Gly Thr Val Cys Asp Pro Ser Arg Ser
Cys Ser Val Ile Glu Asp Asp Gly Leu Gln Ala Ala Phe Thr Thr Ala
His Glu Leu Gly His Val Phe Asn Met Pro His Asp Asp Ala Lys Gln
Cys Ala Ser Leu Asn Gly Val Asn Gln Asp Ser His Met Met Ala Ser
Met Leu Ser Asn Leu Asp His Ser Gln Pro Trp Ser Pro Cys Ser Ala
Tyr Met Ile Thr Ser Phe Leu Asp Asn Gly His Gly Glu Cys Leu Met
Asp Lys Pro Gln Asn Pro Ile Gln Leu Pro Gly Asp Leu Pro Gly Thr
Leu Tyr Asp Ala Asn Arg Gln Cys Gln Phe Thr Phe Gly Glu Asp Ser
Lys His Cys Pro Asp Ala Ala Ser Thr Cys Ser Thr Leu Trp Cys Thr
Gly Thr Ser Gly Gly Val Leu Val Cys Gln Thr Lys His Phe Pro Trp
Ala Asp Gly Thr Ser Cys Gly Glu Gly Lys Trp Cys Ile Asn Gly Lys
Cys Val Asn Lys Thr Asp Arg Lys His Phe Asp Thr Pro Phe His Gly
Ser Trp Gly Pro Trp Gly Pro Trp Gly Asp Cys Ser Arg Thr Cys Gly
Gly Gly Val Gln Tyr Thr Met Arg Glu Cys Asp Asn Pro Val Pro Lys
Asn Gly Gly Lys Tyr Cys Glu Gly Lys Arg Val Arg Tyr Arg Ser Cys
Asn Leu Glu Asp Cys Pro Asp Asn Asn Gly Lys Thr Phe Arg Glu Glu
Gln Cys Glu Ala His Asn Glu Phe Ser Lys Ala Ser Phe Gly Ser Gly
Pro Ala Val Glu Trp Ile Pro Lys Tyr Ala Gly Val Ser Pro Lys Asp
Arg Cys Lys Leu Ile Cys Gln Ala Lys Gly Ile Gly Tyr Phe Phe Val
Leu Gln Pro Lys Val Val Asp Gly Thr Pro Cys Ser Pro Asp Ser Thr
Ser Val Cys Val Gln Gly Gln Cys Val Lys Ala Gly Cys Asp Arg Ile
Ile Asp Ser Lys Lys Lys Phe Asp Lys Cys Gly Val Cys Gly Gly Asn
Gly Ser Thr Cys Lys Lys Ile Ser Gly Ser Val Thr Ser Ala Lys Pro
Gly Tyr His Asp Ile Val Thr Ile Pro Thr Gly Ala Thr Asn Ile Glu
Val Lys Gln Arg Asn Gln Arg Gly Ser Arg Asn Asn Gly Ser Phe Leu
Ala Ile Lys Ala Ala Asp Gly Thr Tyr Ile Leu Asn Gly Asp Tyr Thr
Leu Ser Thr Leu Glu Gln Asp Ile Met Tyr Lys Gly Val Val Leu Arg
Tyr Ser Gly Ser Ser Ala Ala Leu Glu Arg Ile Arg Ser Phe Ser Pro
Leu Lys Glu Pro Leu Thr Ile Gln Val Leu Thr Val Gly Asn Ala Leu
Arg Pro Lys Ile Lys Tyr Thr Tyr Phe Val Lys Lys Lys Glu Ser
Phe Asn Ala Ile Pro Thr Phe Ser Ala Trp Val Ile Glu Glu Trp Gly
Glu Cys Ser Lys Ser Cys Glu Leu Gly Trp Gln Arg Arg Leu Val Glu
Cys Arg Asp Ile Asn Gly Gln Pro Ala Ser Glu Cys Ala Lys Glu Val
Lys Pro Ala Ser Thr Arg Pro Cys Ala Asp His Pro Cys Pro Gln Trp
Gln Leu Gly Glu Trp Ser Ser Cys Ser Lys Thr Cys Gly Lys Gly Tyr
Lys Lys Arg Ser Leu Lys Cys Leu Ser His Asp Gly Gly Val Leu Ser
His Glu Ser Cys Asp Pro Leu Lys Lys Pro Lys His Phe Ile Asp Phe
Cys Thr Leu Thr Gln Cys Ser.

Further, the present invention relates to the variation of proteins which are equivalent to the protein containing the amino acid sequence of SEQ ID NO: 1.

Further, the present invention relates to a protein characterized by containing a matrix metalloproteinase domain, a disintegrin domain, and a thrombospondin domain, except for a mouse ADAMTS-1 protein.

Further, the present invention relates to a gene characterized by encoding the above novel proteins.

Further, the present invention relates to a vector characterized by containing the above gene.

Further, the present invention relates to a transformant characterized by being transformed by the above vector.

Further, the present invention relates to a pharmaceutical composition characterized by comprising (1) the protein containing the amino acid sequence of SEQ ID NO: 1, (2) the variation functionally equivalent to the protein containing the amino acid sequence of SEQ ID NO: 1, or (3) the protein containing a matrix metalloproteinase domain, a disintegrin domain, and a thrombospondin domain.

Further, the present invention relates to an immunologically reactive substance (such as a polyclonal antibody or a monoclonal antibody, or an antibody fragment thereof, or an antiserum) characterized by nature of being capable of specifically reacting with the novel proteins.

Further, the present invention relates to a method for immunologically analyzing the human ADAMTS-1 protein, characterized in that a sample is brought into contact with the immunologically reactive substance, and a complex of the human ADAMTS-1 protein and the immunologically reactive substance is detected.

Further, the present invention relates to a method for analyzing an mRNA of the human ADAMTS-1 protein, characterized in that a sample is brought into contact with a polynucleotide containing a base sequence complementary to that of the mRNA of the human ADAMTS-1 protein consisting of the amino acid sequence of SEQ ID NO: 1, and a complex of the mRNA of the human ADAMTS-1 protein and the polynucleotide is detected.

Further, the present invention relates to a method for extracorporeally detecting an immunological state, characterized by analyzing the human ADAMTS-1 protein or the mRNA thereof.

Further, the present invention relates to an agent for analyzing an immunological state, characterized by containing the immunologically reactive substance capable of immunologically reacting the human ADAMTS-1 protein or the polynucleotide containing the base sequence complementary to that of the mRNA of the human ADAMTS-1 protein.

BRIEF DESCRIPTION OF DRAWINGS

FIG. 2 shows a homology between the mouse ADAMTS-1 gene (SEQ ID NO: 13) and the Flag.1 DNA fragment (SEQ II) NO: 14).

FIG. 5 shows a homology in base sequences of the bases 1 to 480 in the human ADAMTS-1 gene (SEQ ID NO:2) and the mouse ADAMTS-1 gene (SEQ ID NO:13).

FIG. 6 shows a homology in base sequence of the bases 481 to 960 in the human ADAMTS-1 gene (SEQ ID NO:2) and the mouse ADAMTS-1 gene (SEQ ID NO:13).

FIG. 7 shows a homology in base sequence of the bases 961 to 1440 in the human ADAMTS-1 gene (SEQ ID NO:2) and the mouse ADAMTS-1 gene (SEQ ID NO:13).

FIG. 8 shows a homology in base sequence of the bases 1441 to 1920 in the human ADAMTS-1 gene (SEQ ID NO:2) and the mouse ADAMTS-1 gene (SEQ ID NO:13).

FIG. 9 shows a homology in base sequence of the bases 1921 to 2184 in the human ADAMTS-1 gene (SEQ ID NO:2) and the mouse ADAMTS-1 gene (SEQ ID NO:13).

FIG. 10 shows a homology in amino acid sequences of the amino acids 1 to 240 between the human ADAMTS-1 protein (SEQ ID NO:1) and the mouse ADAMTS-1 protein (SEQ ID NO:12).

FIG. 11 shows a homology in amino acid sequences of the amino acids 241 to 510 between the human ADAMTS-1 protein (SEQ ID NO:1) and the mouse ADAMTS-1 protein (SEQ ID NO:12).

FIG. 12 shows a homology in amino acid sequences of the amino acids 511 to 727 between the human ADAMTS-1 protein (SEQ ID NO:1) and the mouse ADAMTS-1 protein (SEQ ID NO:12).

BEST MODE FOR CARRYING OUT THE INVENTION

Figure 1:
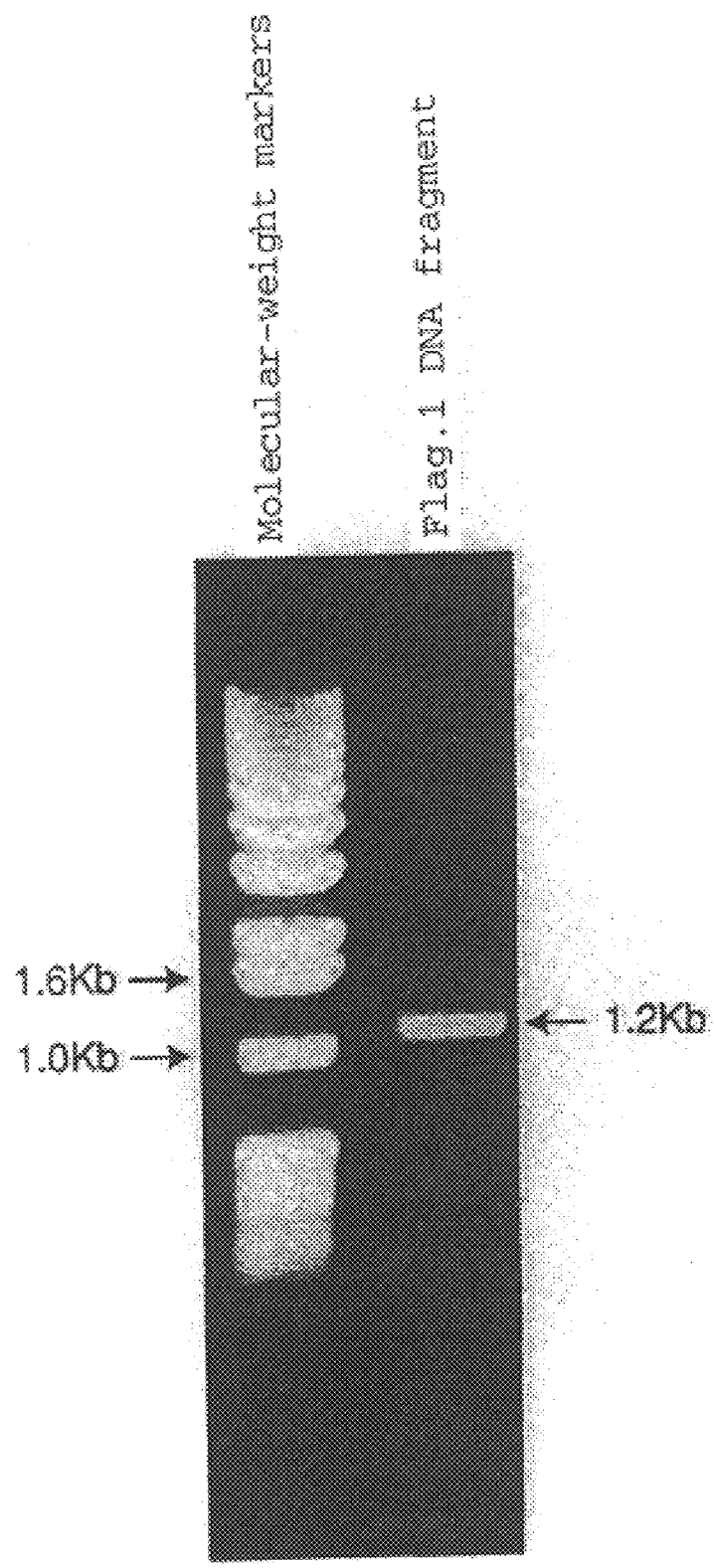
FIG. 1 shows the results of an electrophoresis of a Flag. 1 DNA fragment produced by a PCR.

The present invention will be explained in detail hereinafter.

The human ADAMTS-1 protein of the present invention is a novel protein consisting of 727 amino acid residues; that is, consisting of the amino acid sequence of SEQ ID NO: 1. As shown in FIGS. 10 to 12, the human ADAMTS-1 protein of the present invention contains a matrix metalloproteinase (hereinafter sometimes referred to as "MMP") domain consisting of the 12th to 230th amino acid residues counting from the N-terminal amino acid residue, methionine; a disintegrin (hereinafter sometimes referred to as "DI") domain consisting of the 235th to 305th amino acid residues; and three thrombospondin (hereinafter sometimes referred to as "TSP") domains consisting of the 322nd to 372nd, 618th to 664th, and 672nd to 727th amino acid residues. The human ADAMTS-1 protein contains many arginines and lysines, which are basic amino acids, in a C-terminal region. Therefore, it is believed that the human ADAMTS-1 protein interacts with sulfated polysaccharide molecules, such as heparin or heparan sulfate, in blood.

The novel protein according to the present invention includes the protein containing the amino acid sequence of SEQ ID NO: 1; and a variation functionally equivalent to the protein containing the amino acid sequence of SEQ ID NO:

1 (hereinafter sometimes referred to as a "human ADAMTS-1 protein variation"). The term "human ADAMTS-1 protein variation" as used herein means a protein having an amino acid sequence wherein one or more (particularly one or several) amino acids are deleted in, changed in, or inserted to the amino acid sequence of the human ADAMTS-1 protein, that is, the amino acid sequence of SEQ ID NO: 1, and exhibiting activities of the human ADAMTS-1 protein. A preferable human ADAMTS-1 protein variation has a 92% or more homology in the amino acid sequence with the human ADAMTS-1 protein. The human ADAMTS-1 protein variation includes a fragment which is a part of the protein containing the amino acid sequence of SEQ ID NO: 1 and exhibits the activities of the human ADAMTS-1 protein; and a fragment which is a part of another human ADAMTS-1 protein variation and exhibits the activities of the human ADAMTS-1 protein.

The term "human ADAMTS-1 activity" as used herein means an activity to decrease the numbers of leukocytes and platelets, and at the same time, increase the number of erythrocytes.

Further, the novel protein of the present invention includes a protein containing a matrix metalloproteinase domain, a disintegrin domain, and a thrombospondin domain (hereinafter sometimes referred to as an "ADAMTS protein"). However, the mouse ADAMTS-1 protein is not included in the novel protein of the present invention.

The term "matrix metalloproteinase domain" as used herein means a domain containing an amino acid sequence having a 50% or more (preferably 95% or more) homology with the amino acid sequence of the matrix metalloproteinase domain in the human ADAMTS-1 protein, i.e., the amino acid sequence of the 12th to 230th amino acids in the amino acid sequence of SEQ ID NO: 1.

The term "disintegrin domain" as used herein means a domain containing an amino acid sequence having a 50% or more (preferably 93% or more) homology with the amino acid sequence of the disintegrin domain in the human ADAMTS-1 protein, i.e., the amino acid sequence of the 235th to 305th amino acids in the amino acid sequence of SEQ ID NO: 1.

The term "thrombospondin domain" as used herein means a domain containing an amino acid sequence having a 50% or more homology with at least one of the amino acid sequences of three disintegrin domains in the human ADAMTS-1 protein, that is,
(1) a domain containing an amino acid sequence having a 50% or more (preferably 99% or more) homology with the amino acid sequence of the first thrombospondin domain (hereinafter sometimes referred to as a "human TSP-1 domain") from the N-terminus in the human ADAMTS-1 protein, i.e., the amino acid sequence of the 322nd to 372nd amino acids in the amino acid sequence of SEQ ID NO: 1;
(2) a domain containing an amino acid sequence having a 50% or more (preferably 88% or more) homology with the amino acid sequence of the second thrombospondin domain (hereinafter sometimes referred to as a "human TSP-2 domain") from the N-terminus in the human ADAMTS-1 protein, i.e., the amino acid sequence of the 618th to 664th amino acids in the amino acid sequence of SEQ ID NO: 1; or
(3) a domain containing an amino acid sequence having a 50% or more (preferably 88% or more) homology with the amino acid sequence of the third thrombospondin domain (hereinafter sometimes referred to as a "human TSP-3 domain") from the N-terminus in the human ADAMTS-1 protein, i.e., the amino acid sequence of the 672nd to 727th amino acids in the amino acid sequence of SEQ ID NO: 1.

In the ADAMTS protein of the present invention, the number of each of the matrix metalloproteinase domain, the disintegrin domain, and the thrombospondin domain, and the sequential order thereof, are not particularly limited, so long as at least one matrix metalloproteinase domain, at least one disintegrin domain, and at least one thrombospondin domain are contained at the same time in the ADAMTS protein. A preferred ADAMTS protein contains a matrix metalloproteinase domain, a disintegrin domain and three thrombospondin domains. Further, the sequential order of the domains from the N-terminus to the C-terminus preferably starts from the matrix metalloproteinase domain, followed by the disintegrin domain, and then the thrombospondin domain. When three thrombospondin domains are contained, the sequential order of the domains from the N-terminus to the C-terminus preferably starts from the matrix metalloproteinase domain, followed by the disintegrin domain, and then the first TSP domain, the second TSP domain and the third TSP domain.

In the ADAMTS protein of the present invention, it is preferable that
(1) the matrix metalloproteinase domain has a 95% or more homology in the amino acid sequences with the matrix metalloproteinase domain in the human ADAMTS-1 protein,
(2) the disintegrin domain has a 93% or more homology in the amino acid sequences with the disintegrin domain in the human ADAMTS-1 protein, and
(3) at least one of the thrombospondin domains has a 99% or more homology in the amino acid sequence with the TSP-1 domain in the human ADAMTS-1 protein, an 88% or more homology in the amino acid sequences with the TSP-2 domain in the human ADAMTS-1 protein, or an 88% or more homology in the amino acid sequences with the TSP-3 domain in the human ADAMTS-1 protein.

In the present ADAMTS protein containing three thrombospondin domains, it is preferable that
(3-1) the first thrombospondin domain from the N-terminus has a 99% or more homology in the amino acid sequences with the TSP-1 domain in the human ADAMTS-1 protein,
(3-2) the second thrombospondin domain from the N-terminus has an 88% or more homology in the amino acid sequences with the TSP-2 domain in the human ADAMTS-1 protein, and
(3-3) the third thrombospondin domain from the N-terminus has an 88% or more homology in the amino acid sequences with the TSP-3 domain in the human ADAMTS-1 protein.

The protein of the present invention may be prepared by various known processes. For example, the protein of the present invention may be prepared using a known genetic engineering technique and the gene of the present invention. Alternatively, the protein of the present invention may be purified from a naturally occurring source, using a known protein chemical technique.

The gene of the present invention includes a gene encoding the protein containing the amino acid sequence of SEQ ID NO: 1, particularly the human ADAMTS-1 protein; a gene encoding the human ADAMTS-1 protein variation; and a gene encoding the ADAMTS protein (except the mouse ADAMTS-1 protein). The present gene may be DNA or RNA. The gene encoding the human ADAMTS-1 protein may be, for example, a gene consisting of the base sequence of SEQ ID NO: 2:

```
ATG GAT ATC TGC AGA ATT CGG CTT AGG AAG AAG CGA TTT GTG TCC AGC
CCC CGT TAT GTG AAA ACC ATG CTT GTG GCA GAC CAG TCG ATG GCA GAA
TTC CAC GGC AGT GGT CTA AAG CAT TAC CTT CTC ACG TTG TTT TCG GTG
GCA GCC AGA TTG TAC AAA CAC CCC AGC ATT CGT AAT TCA GTT AGC CTG
GTG GTG GTG AAG ATC TTG GTC ATC CAC GAT GAA CAG AAG GGG CCG GAA
GTG ACC TCC AAT GCT GCC CTC ACT CTG CGG AAC TTT TGC AAC TGG CAG
AAG CAG CAC AAC CCA CCC AGT GAC CGG GAT GCA GAG CAC TAT GAC ACA
GCA ATT CTT TTC ACC AGA CAG GAC TTG TGT GGG TCC CAG ACA TGT GAT
ACT CTT GGG ATG GCT GAT GTT GGA ACT GTG TGT GAT CCG AGC AGA AGC
TGC TCC GTC ATA GAA GAT GAT GGT TTA CAA GCT GCC TTC ACC ACA GCC
CAT GAA TTA GGC CAC GTG TTT AAC ATG CCA CAT GAT GAT GCA AAG CAG
TGT GCC AGC CTT AAT GGT GTG AAC CAG GAT CCC ACA TGA TGG CG TCA
ATG CTT TCC AAC CTG GAC CAC AGC CAG CCT TGG TCT CCT TGC AGT GCC
TAC ATG ATT ACA TCA TTT CTG GAT AAT GGT CAT GG

```
                                        -continued
TGC CGA GAC ATT AAT GGA CAG CCT GCT TCC GAG TGT GCA AAG GAA GTG

AAG CCA GCC AGC ACC AGA CCT TGT GCA GAC CAT CCC TGC CCC CAG TGG

CAG CTG GGG GAG TGG TCA TCA TGT TCT AAG ACC TGT GGG AAG GGT TAC

AAA AAA AGA AGC TTG AAG TGT CTG TCC CAT GAT GGA GGG GTG TTA TCT

CAT GAG AGC TGT GAT CCT TTA AAG AAA CCT AAA CAT TTC ATA GAC TTT

TGC ACA CTG ACA CAG TGC AGT TAA
```

The gene of the present invention, such as the gene consisting of the base sequence of SEQ ID NO: 2, may be obtained, for example, by the following method, which was used by the present inventors when the present gene was obtained for the first time.

That is, various suitable primers for a PCR are prepared on the basis of the base sequence of the mouse ADAMTS-1 gene. DNA fragments may be obtained by carrying out a PCR under a condition milder than that of an ordinary PCR, i.e., at an annealing temperature lower than a usual annealing temperature, using a human kidney cDNA library as templates. Base sequences of the resulting DNA fragments are determined, and compared with the base sequence of the mouse ADAMTS-1 gene, to thereby identify the resulting DNA fragments as the desired genes. Depending on the primers used in the PCR, a full-length human ADAMTS-1 gene or a partial base sequence of the human ADAMTS-1 gene may be obtained. When the partial base sequence is obtained, the remaining base sequence of the gene may be obtained by a RACE (Rapid amplification of cDNA ends) method [Proc Natl. Acad. Sci. USA, 85, 8998–9002 (1988)], and partial base sequences may be ligated by genetic-engineering to obtain the full-length base sequence.

When the present inventors designed the base sequences of the primers used to obtain the gene in the above method for the first time, the base sequence of the human ADAMTS-1 gene was not known. Therefore, it was almost impossible to select base sequences having a complete homology between the mouse ADAMTS-1 gene and the human ADAMTS-1 gene.

The present inventors used primers designed on the basis of the base sequence of the mouse ADAMTS-1 gene to carry out a PCR at a usual temperature, but a desired DNA fragment could not be obtained. However, the present inventors used the same primers and carried out a PCR under a condition milder than that of an ordinary PCR, i.e., an annealing temperature was set lower than a usual annealing temperature, whereby the desired DNA fragment was able to be obtained. The comparison of the base sequence of the resulting human ADAMTS-1 gene with the base sequences of the primers used revealed an insufficient homology.

At present, the base sequence of the human ADAMTS-1 gene has been determined according to the present invention. Therefore, the base sequence of the human ADAMTS-1 gene may be used to design primers for a PCR or probes for plaque hybridization. Such primers or probes may be used to obtain the gene of the present invention by a known method to obtain a gene, such as a PCR under ordinary conditions or plaque hybridization, instead of the method used by the present inventors to obtain the present gene for the first time.

The present inventors attempted to obtain an unknown human ADAMTS-1 gene from the human kidney cDNA library by plaque hybridization, using probes designed on the basis of the base sequence of the known mouse ADAMTS-1 gene, but a desired gene was not obtained. One of the reasons of this failure was an insufficient homology of the probes used. Further, the present inventors have carried out northern hybridization to analyze the mRNA of the human ADAMTS-1 protein, and confirmed that the failure must also have occurred because mRNA is expressed in a very small amount, and thus a very small number of the human ADAMTS-1 genes are copied in a cDNA library.

The gene of the present invention may be obtained by plaque hybridization, using probes designed on the basis of the base sequence of the human ADAMTS-1 gene.

The resulting gene of the present invention may be expressed in, for example, a eucaryotic or procaryotic host to produce the protein of the present invention.

If a DNA fragment containing a desired gene is directly introduced into a host cell, the fragment is not reproduced. However, an extrachromosomal gene reproducible in a cell, such as a plasmid, may be used as a vector to prepare an expression plasmid. A vector which may be used preferably contains genetic information necessary for replication in a host cell, can be independently replicated, is easily isolated and purified from a host cell, and contains a detectable marker.

An expression vector containing the DNA of the present invention may be constructed in accordance with a host cell from various commercially available vectors. A method for introducing the DNA into the vector is well known.

As a procaryotic host, there may be mentioned, for example, E. coli strains, such as XL1-Blue, HB101, JM109, DH5α, AG-1, K12 strain 294 (ATCC 31446), B, χ1776 (ATCC 31537), C600, or W3110 (F-, λ-, prototrophic; ATCC 27375). Further, Bacillus strains, such as Bacillus subtibis, enteric bacteria, such as Salmonella typhimurium or Serratia marcescens, or Pseudomonas strains may be used.

When the procaryotic host is used, an expression plasmid which may be used as a vector contains a promoter, an SD base sequence, and a base sequence necessary for initiating a protein synthesis, i.e., ATG, upstream of the gene of the present invention so as to express the gene. As a vector for E. coli strains, pUC19, pBR322, or pBR327 are generally and widely used.

As a promoter, for example, triptophan promoter, $P_L$ promoter, lac promoter, tac promoter, trc promoter, lpp promoter, or β-lactamase promoter may be used. Examples of the marker gene are an ampicillin resistance gene or tetracycline resistance gene.

As a eucaryotic host, a yeast is generally and widely used. Of the yeasts, a Saccharomyces yeast can be advantageously used. As an expression vector for the eucaryotic host such as a yeast, for example, YRp7 may be used As a promoter of the expression vector for a yeast expression, for example, alcohol dehydrogenase (ADH), GAL10, 3-phosphoglycerate kinase, enolase, glyceraldehyde-3-phosphate dehydrogenase, or hexokinase may be used. An example of a marker gene is a trpl gene.

As a replication origin, a stop codon, or other DNA sequences used to control a transcription or translation in a yeast cell, usual known DNA sequences suitable to the yeast cell may be used.

As a culture cell host of a higher animal, there may be mentioned, for example, a rhesus renal cell, a mosquito larva cell, an African Green Monkey kidney cell (COS-7 or COS-1), a murine fetal fibroblast, a Chinese hamster ovary cell or a dihydrofolate reductase-defective strain thereof, a human cervical epitheliocyte, a human fetal kidney cell, a moth ovary cell, a human myeloma cell, or a murine fibroblast cell.

The vector generally contains functional sequences to express the DNA of the present invention in a host cell, for example, a replication origin, a promoter, which should be upstream of the DNA of the present invention, a ribosome binding site, a polyadenylated site, and/or a transcription termination sequence. A preferable promoter is, for example, an adenovirus 2 main late promoter, SV40 early promoter, SV40 late promoter, or a promoter from cytomegalovirus, Rous sarcoma virus, or an eucaryote gene, such as estrogen inducible chick egg albumin gene, interferon gene, glucocorticoid inducible throsine aminotransferase gene, thymidine kinase gene, main early and late adenovirus gene, phosphoglycerate kinase gene, or α factor gene.

A replication origin from adenovirus, SV40, bovine papilloma virus (BPV), vesicular stomatitis virus (VSV), or a derivative vector thereof may be used as the replication origin. In these cases, for example, a neomycin resistance gene, a methotrexate resistant dihydrofolate reductase (DHR) gene, or a blasticidin S resistance gene may be used as the marker gene.

As an insect cell host, for example, BmN4 cell, Sf9 cell, Sf21 cell, or an ovary cell of Trichoplusiani may be used. Further, a larval silkworm individual may be used as a host. A gene transfer to the insect cell can be carried out by co-infecting the insect cell with a virus DNA and a transfer vector containing a desired gene to be incorporated. As the virus DNA, for example, a Bombyx mori nuclear polyhedrosis virus, or Autographica californica multiple nuclear polyhedrosis virus may be used. As the transfer vector containing the desired gene to be inserted, for example, a polyhedrin promoter or p10 promoter vector may be used. The desired gene can be inserted downstream of the promoters. The transfer vector can be replicated in E. coli, but cannot be replicated in an insect cell. Therefore, it is preferable to replicate many vectors in E. coli, and then express them in the insect cell. According to this process, a larger amount of expressed substances can be recovered in comparison with an animal cell.

The resulting expression plasmid may be transfected into an appropriate host cell, for example, a microorganism cell, such as E. coli yeast, or an animal cell, to produce the transformant of the present invention. The method for transfecting the DNA may be, for example, a method of utilizing a competent cell treated with calcium chloride, a protoplast method, a calcium phosphate transfection method, or an electroporation method.

The pharmaceutical composition of the present invention comprises (1) the protein containing the amino acid sequence of SEQ ID NO: 1, particularly the human ADAMTS-1 protein, (2) the human ADAMTS-1 protein variation, or (3) the ADAMTS protein, as an active ingredient. In the pharmaceutical composition of the present invention, the active ingredient may be the mouse ADAMTS-1 protein. The proteins which may be used as the active ingredient of the pharmaceutical composition in the present invention have activities to influence hematopoietic functions, for example, activities to decrease the number of leukocytes and platelets, and at the same time, increase the number of erythrocytes, when administered into a blood vessel.

It is possible to orally or parenterally administer the pharmaceutical composition according to the present invention, i.e., the protein containing the amino acid sequence of SEQ ID NO: 1, particularly the human ADAMTS-1 protein, the human ADAMTS-1 protein variation, or the ADAMTS protein, alone or preferably together with a pharmaceutically or veterinarily acceptable ordinary carrier, to an animal, preferably a mammal, particularly humans. The formulation is not particularly limited to, but may be, for example, oral medicines, such as powders, fine subtilaes, granules, tablets, capsules, suspensions, emulsions, syrups, extracts or pills, or parenteral medicines, such as injections, liquids for external use, ointments, suppositories, creams for topical application, or eye lotions.

The oral medicines may be prepared by an ordinary method using, for example, fillers, binders, disintegrating agents, surfactants, lubricants, flowability-enhancers, diluting agents, preservatives, coloring agents, perfumes, tasting agents, stabilizers, humectants, antiseptics, antioxidants, such as gelatin, sodium alginate, starch, corn starch, saccharose, lactose, glucose, mannitol, carboxylmethylcellulose, dextrin, polyvinyl pyrrolidone, crystalline cellulose, soybean lecithin, sucrose, fatty acid esters (such as glycerin fatty acid ester, sucrose fatty acid ester, sorbitan fatty acid ester, or propyleneglycol fatty acid ester), talc, magnesium stearate, polyethylene glycol, magnesium silicate, silicic anhydride, or synthetic aluminum silicate.

For the parenteral administration, for example, an injection such as a subcutaneous or intravenous injection, or the per rectum administration may be used. Of the parenteral formulations, an injection is preferably used.

When the injections are prepared, for example, water-soluble solvents, such as physiological saline or Ringer's solution, water-insoluble solvents, such as plant oil or fatty acid ester, agents for rendering isotonic, such as glucose or sodium chloride, solubilizing agents, stabilizing agents, antiseptics, suspending agents, or emulsifying agents may be optionally used, in addition to the protein containing the amino acid sequence of SEQ ID NO: 1, particularly the human ADAMTS-1 protein, the human ADAMTS-1 protein variation, or the ADAMTS protein.

The pharmaceutical composition may be administered in the form of a sustained release preparation using sustained release polymers. For example, the pharmaceutical composition of the present invention may be incorporated to a pellet made of ethylenevinyl acetate polymers, and the pellet may be surgically implanted in a tissue to be treated.

The pharmaceutical composition of the present invention may contain the protein containing the amino acid sequence of SEQ ID NO: 1, particularly the human ADAMTS-1 protein, the human ADAMTS-1 protein variation, or the ADAMTS protein in an amount, but not particularly limited to, of 0.0001 to 99% by weight, preferably 0.01 to 80% by weight, more preferably 0.01 to 50% by weight.

When the pharmaceutical composition of the present invention is utilized, the dose is not particularly limited, but varies with the kind of disease, the age, sex, body weight, or symptoms of the subject, a method of administration, or the like. However, the protein containing the amino acid sequence of SEQ ID NO: 1, particularly the human ADAMTS-1 protein, the human ADAMTS-1 protein variation, or the ADAMTS protein may be orally or parenterally administered at a dosage of about 0.0001 µg/kg to 10,000 µg/kg, preferably 0.001 µg/kg to 1,000 µg/kg, more preferably 0.01 µg/kg to 100 µg/kg a day for an adult, usually once or divided into up to four dosages.

The pharmaceutical composition of the present invention may be used not only for the pharmaceutical application but also for various applications. That is, the protein containing the amino acid sequence of SEQ ID NO: 1, particularly the human ADAMTS-1 protein, the human ADAMTS-1 protein variation, or the ADAMTS protein may be administered in the form of functional food or health food, together with a conventional food additive, or directly added to food as a food additive.

The pharmaceutical composition of the present invention contains the protein containing the amino acid sequence of SEQ ID NO: 1, particularly the human ADAMTS-1 protein, the human ADAMTS-1 protein variation, or the ADAMTS protein, and thus is useful as, for example, an agent for reducing leukocytes, an agent for reducing platelets, or an agent for increasing erythrocytes.

It is generally known that, when inflammation occurs, leukocytes are activated in blood, move to an inflamed site, evolute and/or cause pathosis. Therefore, it is believed that the human ADAMTS-1 protein of the present invention would be effective in the treatment of various inflammatory diseases, such as rheumatic arthritis, psoriasis, asthma, hepatitis, Kawasaki disease, gout, adult respiratory distress syndrome (ARDS), Crohn's disease, ulcerative colitis, sepsis, or nephritis. Further, the human ADAMTS-1 protein of the present invention exhibits a function to decrease the number of leukocytes and platelets, and thus would be effective in a treatment of true hypervolemia. The human ADAMTS-1 protein of the present invention exhibits a function to decrease the number of platelets. Therefore, it is believed that the human ADAMTS-1 protein of the present invention would exhibit an anti-thrombotic action, and would be effective in the treatment of cardiac infarction, cerebral inferction, or multi-organ failure. The human ADAMTS-1 protein of the present invention exhibits a function to significantly increase the number of erythrocytes, and would be effective in a treatment of anemia, as erythropoietin.

When lipopolysaccharide (LPS), an immunologically stimulating substance, is administered to a mouse (for example, a 10 µg/mouse), an expression of the mouse ADAMTS-1 gene is superinduced in a heart and a kidney [J. Biol. Chem., 272, 556–562 (1997)]. Therefore, the mouse ADAMTS-1 protein would possibly exhibit a protective function for a heart and a kidney, upon a lethally acute inflammation such as an endotoxin shock.

Thrombospondin (TSP) is known as a factor for inhibiting vascularization, i.e., specifically inhibiting a growth of endothelial cells [J. Cell. Biol., 111, 765–772 (1990)]. Further, it was reported that the proliferation and metastasis of cancer cells can be inhibited by the induction of TSP in cancer cells [J. Cell. Biol., 111, 765–772 (1990)]. Therefore, the human ADAMTS-1 protein would probably show a function for inhibiting a cancer or metastasis. Further, a recent report had stated that TSP or disintegrin is involved in a bone formation [Biochem. Biophy. Res. Commun., 213, 1017–1025 (1995)]. Therefore, the human ADAMTS-1 protein could be applicable to the treatment of a metabolic bone disease, such as osteoporosis.

The immunologically reactive substance of the present invention specifically reacts the protein containing the amino acid sequence of SEQ ID NO: 1, particularly the human ADAMTS-1 protein, the human ADAMTS-1 protein variation, or the ADAMTS protein. The immunologically reactive substance of the present invention includes, for example, an antibody (a monoclonal antibody or a polyclonal antibody), fragments of the antibody, such as, Fab, Fab', F(ab')$_2$, or Fv, and an antiserum. The immunologically reactive substance of the present invention specifically reacts the human ADAMTS-1 protein, and therefore, the immunologically reactive substance of the present invention specifically reacts the human ADAMTS-1 protein, and therefore, is useful for analyzing the human ADAMTS-1 protein by immunological ways.

The monoclonal antibody of the present invention may be prepared by a known method, for example, the following method.

A physiological salt solution containing an antigen is mixed with an equal volume of complete Freund's adjuvant or incomplete adjuvant, or an equivalent thereof, such as Hunter's TiterMax™ (Funakoshi; Cat. No. YT001-00, Tokyo, Japan), until emulsified. The resulting emulsion is administered subcutaneously, intraperitoneally, intravenously, intramuscularly, or intradermally to a mammal, for example, a mouse, rat, rabbit, or hamster, more particularly, a mouse, such as a BALB/c mouse, selected in view of a congeniality to a conventional myeloma cell (a first immunization). Then, the same procedure is repeated at intervals of two to four weeks for several immunizations, and final immunization is carried out using only the antigen solution. The spleens are removed aseptically several days after the final immunization, and spleen cells are prepared.

The resulting spleen cells are used for a cell fusion. The other parent cells used for the cell fusion, that is, the myeloma cells, may be known cell lines, such as, P3X63-Ag8(X63) [Nature, 256, 495–497 (1975)], P3X63-Ag8U1 (P3U1) [Current Topics in Microbiology and Immunology, 81, 1–7 (1978)], or P3X63Ag8.653 (ATCC deposition No. CRL-1580).

The cell fusion may be carried out by ususal methods, for example, the method of Milstein et. al. [Methods in Enzymology, 73, 3–47 (1981)]. The resulting hybridomas are administered to mammals (for example, mice), and desired monoclonal antibodies are separated and purified from ascites of the mammals. The separation and purification method used may be a known method, such as a dialysis ion exchange chromatography using an ammonium sulfate; an affinity column chromatography using a protein A or protein G binding polysaccharides carrier or an anti-mouse immunoglobrin antibody binding polysaccharides carrier; dialysis, or lyophilization.

The polyclonal antibody of the present invention may be prepared by a known method, as indicated below. That is, a physiological salt solution containing an antigen is mixed with an equal volume of complete Freund's adjuvant or incomplete adjuvant, or an equivalent thereof, such as Hunter's TiterMax™ (Funakoshi; Cat. No. YT001-00, Tokyo, Japan), until emulsified. The resulting emulsion is administered subcutaneously, intraperitoneally, or intramuscularly to a mammal, for example, a rabbit, or goat (a first immunization). Then, the same procedure is repeated at intervals of two to four weeks for several immunizations. One or two weeks after a final immunization, blood is taken from a carotid artery or a heart of the mammal, and salted-out with ammonium sulfate to prepare a serum.

The antibody fragment of the present invention may be prepared, for example, by digesting the polyclonal antibody or monoclonal antibody of the present invention with a known protease by a conventional method, and then isolating and purifying by a conventional method.

Production of the human ADAMTS-1 protein is facilitated by an immunologically stimulating substance, such as LPS, and therefore, the human ADAMTS-1 protein may be used as a diagnostic marker of an immunological state in a method for extracorporeally detecting the immunological state. More particularly, the extracorporeally detecting method of the present invention may be applied to a sample taken from a subject to be examined, to thereby detect an immunological state of an immune function of the subject, when the immune function is affected by various diseases, such as inflammation, cancer, cachexia, such as cancer cachexia or infectious disease-related cachexia, infectious disease, or leukemia. If the immune function of the subject is normal, an immunological state corresponding to the immune function can be detected.

The sample which may used in the present invention is not particularly limited, so long as it has a possibility of including the human ADAMTS-1 protein. The sample may be a biological sample taken from a human, particularly a patient, for example, a humor, such as a tissue (e.g., cells) or an extract therefrom, blood, such as serum, and plasma, urine, or cerebrospinal fluid. A sample used in a conventional clinical examination may be used in the present invention without limitation.

In the analysis step of the human ADAMTS-1 protein in the sample, the sample is first brought into contact with the substance immunologically reactive to the human ADAMTS-1 protein. If the sample does not contain the human ADAMTS-1 protein, a reaction with the immunologically reactive substance does not occur. If the sample contains the human ADAMTS-1 protein, the immunologically reactive substance binds the human ADAMTS-1 protein, and a complex of the immunologically reactive substance and the human ADAMTS-1 protein is formed in an amount correlated with that of the human ADAMTS-1 protein present in the sample. The complex may be easily detected by a known method, and therefore, an existence of the human ADAMTS-1 protein in the sample can be detected by detecting the existence of the complex, or an amount of the human ADAMTS-1 protein in the sample can be measured by measuring the amount of the complex. The human ADAMTS-1 protein in a tissue or a cell may be measured, using a tissue section sample or a cell sample in a fluorescent antibody technique or an enzyme antibody technique.

The immunologically reactive substance capable of immunologically reacting the human ADAMTS-1 protein includes an anti-human ADAMTS-1 protein antiserum, an anti-human ADAMTS-1 protein polyclonal antibody, of an anti-human ADAMTS-1 protein monoclonal antibody, or a fragment thereof. The immunologically reactive substance may be used singly or in combination thereof. The fragment includes, for example, Fab, Fab', F(ab')$_2$, or Fv.

In the method for immunologically analyzing the human ADAMTS-1 protein according to the present invention, the sample is brought into contact with the immunologically reactive substance capable of immunologically reacting the human ADAMTS-1 protein, and a complex of the human ADAMTS-1 protein and the immunologically reactive substance is formed. Then, the human ADAMTS-1 protein bound to the antibody is detected and the amount thereof is measured by an immunochemical method, to thereby find a level of the human ADAMTS-1 protein in the sample.

The immunochemical method principally may be, for example, any conventional immunoassay, for example, EIA, ELISA, RIA or the like. The immunochemical methods are generally classified as follows:

(1) Competitive Assay

A sample containing an unknown amount of antigens and a given amount of labeled antigens is competitively reacted with a given amount of antibodies, and then an activity of the labeled antigens bound to the antibodies or an activity of the labeled antigens not bound to the antibodies is measured.

(2) Sandwich Assay

An excess amount of antibodies immobilized on carriers is added and reacted to a sample containing an unknown amount of antigens (a first reaction). Then, a given excess amount of labeled antibodies is added and reacted therewith (a second reaction). An activity of the labeled antibodies on the carriers is measured. Alternatively, an activity of the labeled antibodies which are not on the carriers is measured. The first reaction and the second reaction may be carried out at the same time, or sequentially.

When a labeling agent is a radioactive isotope, a well counter or a scintillation counter may be used for measurement. When the labeling agent is an enzyme, an enzymatic activity can be measured by colorimetry or fluorimetry, after adding a substrate and allowing to stand. When the labeling agent is a fluorescent substance or an luminescent substance, a known method therefor may be used, respectively.

In addition to the above methods, recently a western blotting method has been used wherein electrophoresed proteins are transferred onto a filter such as a nitrocellulose membrane, and a target protein is detected with an antibody. The western blotting method may also be used in the detection of the human ADAMTS-1 protein in the present invention.

The antibody used in the above methods can be labeled with an appropriate marker. Examples are a radioactive isotope, an enzyme, a fluorescent substance, or a luminescent substance, by a known method of labeling antibodies.

The radioactive isotope may be, for example, $^{125}$I, $^{131}$I, $^{3}$H, $^{14}$C, or $^{35}$S.

Preferably, the enzyme used is stable and has a large specific activity. Examples of the enzyme are a glycosidase (such as, β-galactosidase, β-glucosidase, β-glucuronidase, β-fructosidase, α-galactosidase, α-glucosidase, or α-mannosidase), an amylase (such as, α-amylase, β-amylase, isoamylase, glucoamylase, or taka-amylase), a cellulase, or a carbohydrase such as lysozyme; a urease, or an amidase such as asparaginase; a choline esterase, such as acetylcholinesterase, a phosphatase, such as alkaline phosphatase, a sulfatase, an esterase such as lipase; a nuclease such as deoxyribonuclease or ribonuclease; an iron porphyrin enzyme, such as a catalase, peroxidase or cytochrome oxidase; a copper enzyme, such as a tyrosinase or ascorbate oxidase; dehydrogenase, such as an alcohol dehydrogenase, malate dehydrogenase, lactate dehydrogenase, or isocitrate dehydrogenase.

The fluorescent substance may be, for example, fluorescamine, or a fluorescence isothiocyanate, and the luminescent substance may be, for example, luminol, a luminol derivative, luciferin or lucigenin. A signal from the above label may be detected by known methods.

The labeling agent can be bound to antibodies by any conventional method, such as a chloramin T method [Nature, 194, 495–496, (1962)], a periodic acid method [Journal of Histochemistry and Cytochemistry, 22, 1084–1091, (1974)], or a maleimide method [Journal of Biochemistry, 79, 233–236, (1976)].

An EIA method as one of the above measurement methods will be mentioned hereinafter. A sample is added to the first anti-human ADAMTS-1 protein antibodies immobilized on a carrier (such as an assay plate), and the anti-human ADAMTS-1 protein antibodies are bound to the human ADAMTS-1 proteins to form complexes. To the complexes, the second anti-human ADAMTS-1 protein antibodies labeled with enzyme (such as peroxidase) are added to react with the complexes to form "first antibody/human ADAMTS-1 protein/second antibody" complexes. To the resulting "first antibody/human ADAMTS-1 protein/second antibody" complexes, a substrate for the enzyme label (such as peroxidase) is added, and an absorbance or fluorescent strength of products of the enzymatic reaction is measured, whereby enzymatic activities of the enzyme labels attached to the "first antibody/human ADAMTS-1 protein/second antibody" complexes are measured. A series of the above procedures is carried out in advance for a standard solution containing a known amount of the human ADAMTS-1 protein, and a standard curve based on the relationship between the human ADAMTS-1 protein and the absorbance or fluorescent strength is prepared. A comparison is made between the standard curve and absorbance or fluorescent strength for a sample containing an unknown amount of the human ADAMTS-1 proteins, and the amount of the human ADAMTS-1 proteins in the sample can be measured.

Another EIA method will be mentioned hereinafter. A sample is brought into contact with a carrier (such as an assay plate) to immobilize the human ADAMTS-1 proteins in the sample onto the carrier. Then, the anti-human ADAMTS-1 protein antibodies (first antibodies) are added thereto to form complexes of the human ADAMTS-1 protein and the first antibody. To the complexes are added anti-first antibody antibodies (second antibodies) labeled with enzyme (such as peroxidase), to react with the complexes to form "human ADAMTS-1 protein/first antibody/second antibody" complexes. To the resulting "human ADAMTS-1 protein/first antibody/second antibody" complexes is added a substrate for the enzyme label (such as peroxidase), and the absorbance or fluorescent strength of products of the enzymatic reaction is measured, whereby enzymatic activities of the enzyme labels attached to the "human ADAMTS-1 protein/first antibody/second antibody" complexes are measured. A series of the above procedures is carried out in advance for a standard solution containing a known amount of the human ADAMTS-1 protein, and a standard curve based on the relationship between the human ADAMTS-1 protein and the absorbance or fluorescent strength is prepared. A comparison is made between the standard curve and the absorbance or fluorescent strength for a sample containing an unknown amount of the human ADAMTS-1 proteins, and the amount of the human ADAMTS-1 proteins in the sample can be measured.

Further, an RIA method will be mentioned hereinafter. A sample is added to the first anti-human ADAMTS-1 protein antibodies immobilized on a carrier (such as a test tube), and the anti-human ADAMTS-1 protein antibodies are bound to the human ADAMTS-1 proteins to form complexes. To the complexes are added the second anti-human ADAMTS-1 protein antibodies labeled with radioactive isotope (such as $^{125}$I), to react with the complexes to form "first antibody/human ADAMTS-1 protein/second antibody" complexes. A radioactivity of the resulting "first antibody/human ADAMTS-1 protein/second antibody" complexes is measured. A series of the above procedures is carried out in advance for a standard solution containing a known amount of the human ADAMTS-1 protein, and a standard curve based on the relationship between the human ADAMTS-1 protein and the radioactivity is prepared. A comparison is made between the standard curve and the radioactivity for a sample containing an unknown amount of the human ADAMTS-1 proteins, and the amount of the human ADAMTS-1 proteins in the sample can be measured.

Another RIA method will be mentioned hereinafter. A sample is brought into contact with a carrier (such as a test tube) to immobilize the human ADAMTS-1 proteins in the sample onto the carrier. Then, the anti-human ADAMTS-1 protein antibodies (first antibodies) are added thereto to form complexes of the human ADAMTS-1 protein and the first antibody. To the complexes are added anti-first antibody antibodies (second antibodies) labeled with radioactive isotope (such as $^{125}$I), to react with the complexes to form "human ADAMTS-1 protein/first antibody/second antibody" complexes. A radioactivity of the resulting "human ADAMTS-1 protein/first antibody/second antibody" complexes is measured. A series of the above procedures is carried out in advance for a standard solution containing a known amount of the human ADAMTS-1 protein, and a standard curve based on the relationship between the human ADAMTS-1 protein and the radioactivity is prepared. A comparison is made between the standard curve and the radioactivity for a sample containing an unknown amount of the human ADAMTS-1 proteins, and the amount of the human ADAMTS-1 proteins in the sample can be measured.

In the method for analyzing the mRNA of the human ADAMTS-1 protein in a sample, the sample is reacted with a polynucleotide containing a base sequence complementary to that of the mRNA of the human ADAMTS-1 protein, and the resulting complex of the mRNA of the human ADAMTS-1 protein and the polynucleotide is detected, or the amount of the complex is measured to thereby analyze the mRNA of the human ADAMTS-1 protein.

The polynucleotide contains a sequence complementary or substantially complementary to that of a part of the mRNA transcribed from a selected gene (DNA), and thus forms a double strand with the mRNA transcribed from the target gene. It is believed that any polynucleotide sufficiently complementary to form a stable complex with a target mRNA can be used. The polynucleotide able to be used in the present invention may be complementary to substantially any region in a target mRNA. The polynucleotide can be used as a DNA probe for detecting an increase or a decrease of expression of the mRNA specific to the human ADAMTS-1 protein gene. That is, the polynucleotide is specifically attached to the mRNA of the target human ADAMTS-1 protein, and forms a molecular hybrid, whereby a degree of expression of the human ADAMTS-1 protein in cells can be detected.

The polynucleotide able to be used in the present invention may be prepared by appropriately selecting a base sequence complementary to a specific base sequence of the mRNA of the target human ADAMTS-1 protein, and using a known DNA synthesizer, a known PCR apparatus, a gene cloning or the like. Various length polynucleotides may be used, but the polynucleotide preferably has 10 or more bases, more preferably 17 or more bases.

The polynucleotide may be a non-modified polynucleotide or a polynucleotide analogue. An appropriate analogue may be, for example, an ethyl or methyl phosphate analogue, or a phosphorothioated polydeoxynucleotide [Nucleic Acids Res., 14, 9081–9093, (1986); J. Am. Chem. Soc., 106, 6077–6079, (1984)], with recent improvement in the production of polynucleotide analogue, for example, a 2'-O-methylribonucleotide [Nucleic Acids Res., 15, 6131–6148, (1987)], or a conjugated RNA-DNA analogue, i.e., chimera polynucleotide [FEBS Lett., 215, 327–330, (1987)], may be used.

The selected polynucleotide may be of any kind, for example, may have an electrical charge or no electrical charge. The polynucleotide may be labeled with a known labeling agent, such as a radioactive isotope, or a fluorescent substance by a conventional method, so as to carry out the above experiment in vitro or in vivo. The radioactive isotope may be, for example, $^{125}$I, $^{131}$I, $^{3}$H, $^{14}$C, $^{32}$P, or $^{35}$S. Of these radioactive isotopes, it is preferable to label the polynucleotide with $^{32}$P by a random primer method [Anal. Biochem., 132, 6–13, (1983)]. Further, a fluorescent coloring agent forming a derivative may be used as a labeling agent, as this enables an easy handling with a low risk factor. As the fluorescent coloring agent, any coloring agents capable of binding the polynucleotide may be used. For example, fluorescein, rhodamin, Texas red, 4-fluoro-7-nitrobenzofurazane (NBD), coumarin, fluorescamine, succinyl fluorescein, or dansyl may be preferably used.

An amount of an mRNA of the human ADAMTS-1 protein may be measured by a northern blotting method, using cDNA of the human ADAMTS-1 protein as follows: an mRNA is extracted and isolated from any somatic cell or tissue, then the isolated mRNA is electrophoresed on an agarose gel and transferred onto a nitro cellulose or nylon membrane, and then reacted with a labeled human ADAMTS-1 protein cDNA probe to measure an amount of the mRNA of the human ADAMTS-1 protein. The human ADAMTS-1 protein cDNA probe used is a DNA complementary to the human ADAMTS-1 protein mRNA, and has preferably 17 or more bases.

The agent for analyzing an immunological state according to the present invention contains, as a main ingredient, the immunologically reactive substance capable of immunologically reacting the human ADAMTS-1 protein. The immunologically reactive substance capable of immunologically reacting the human ADAMTS-1 protein may be, for example, an anti-human ADAMTS-1 protein antiserum, an anti-human ADAMTS-1 protein polyclonal antibody, or an anti-human ADAMTS-1 protein monoclonal antibody, of a fragment of the antibodies.

The agent for analyzing an immunological state according to the present invention may contain, as a main ingredient, the polynucleotide containing the base sequence complementary to that of an mRNA of the human ADAMTS-1 protein, instead of the immunologically reactive substance.

The human ADAMTS-1 protein per se or an mRNA of the human ADAMTS-1 protein in a sample can be analyzed according to the above methods using the agent for analyzing an immunological state according to the present invention, and the immunological state of a subject to be examined, wherein the immune function is affected by various diseases, can be judged from the result.

EXAMPLES

The present invention now will be further illustrated by, but is by no means limited to, the following Examples.

Example 1

Isolation of the Human ADAMTS-1 cDNA and Determination of the Base Sequence Thereof As primers for a PCR method, a DNA [hereinafter referred to as a "forward primer (1)"] having the base sequence (i.e., the base sequence of SEQ ID NO: 4: AGAACCTGTG GTGGTGGAGT TCAATACACA) corresponding to an amino acid sequence (i.e., the amino acid sequence of SEQ ID NO: 3: Arg Thr Cys Gly Gly Gly Val Gln Tyr Thr) contained in the first thrombospondin (TSP) domain from the N-terminus among three TSP domains of the mouse ADAMTS-1 protein [J. Biol. Chem., 272, 556–562 (1997)], and a DNA [hereinafter referred to as a "back primer (1)"] having the base sequence (i.e., the base sequence of SEQ ID NO: 5: CCTCTTAACT GCACTGTGTC AGTGTGCAAA AG) complementary to the base sequence encoding amino acids in the C-terminus of the mouse ADAMTS-1 protein and the base sequence in the vicinal regions (i.e., the regions upstream and downstream of the C-terminus) were chemically synthesized.

To 99 µl of a solution containing 0.5 µM forward primer (1), 0.5 µM back primer (1), 0.5 units of Taq polymerase (Ex Taq polymerase; Takarashuzo, Kyoto, Japan), and 40 µM 4dNTP in a PCR buffer [10 mM Tris-HCl (pH 8.3), 50mM KCl] (Ex Taq buffer; Takarashuzo, Kyoto, Japan), 1 µl of a human kidney cDNA library (Marathon-Ready cDNA; Clontech Lab. Inc., Palo Alto, Calif., USA) was added as a template DNA. A PCR method was performed at an annealing temperature lower than that used in a standard PCR method. That is, the PCR reaction was carried out by repeating a cycle composed of denaturation at 94° C. for 30 seconds, annealing at 50° C. for 30 seconds, and DNA synthesis at 72° C. for 2 minutes, 40 times, i.e., 40 cycles.

A sample (5 µl) was taken from the resulting reaction mixture, and electrophoresed on 1% agarose gel. As shown in FIG. 1, a single DNA band of 1.2 Kb was observed. The rest of the reaction mixture was electrophoresed, and the DNA fragment of 1.2 Kb (hereinafter sometimes referred to as a "Flag. 1 DNA fragment") was recovered from a low-melting-point agarose gel. Then, the Flag. 1 DNA fragment was cloned in a pCR™ 2.1 vector (Invitrogen Corp., San Diego, Calif., USA).

A part (303 bp) of the base sequence of the cloned Flag. 1 DNA fragment (SEQ ID NO: 14) was determined by an automatic DNA sequencer (DSQ1000; Shimadzu Corp., Kyoto, Japan). A homology search between the partial base sequence of the cloned Flag. 1 DNA fragment and the base sequence of the mouse ADAMTS-1 was conducted to find that a homology in the base sequences was 77.4%. The partial base sequence of the Flag. 1 DNA fragment and a partial base sequence of the mouse ADAMTS-1 gene having a homology therewith are shown in FIG. 2. The symbol ":" in FIG. 2 means that a base in the Flag. 1 DNA fragment is identical to a corresponding base in the mouse ADAMTS-1 gene.

Figure 3:
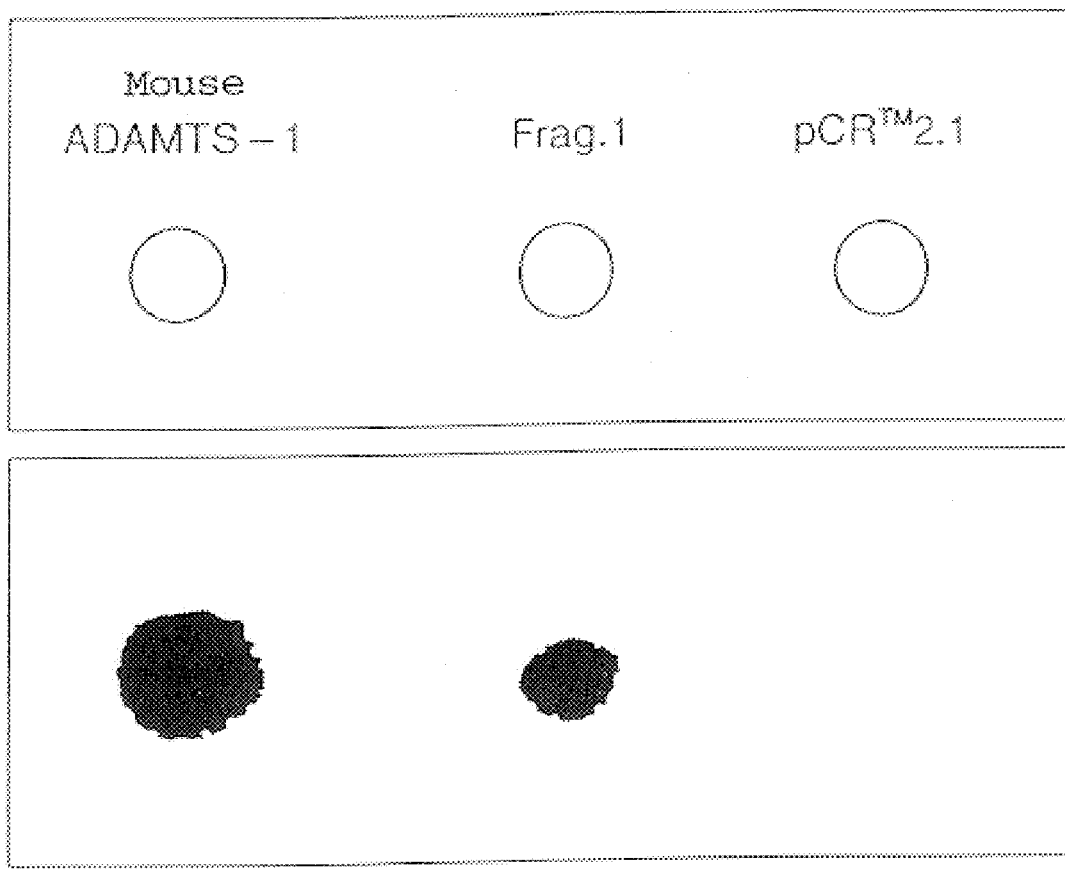
FIG. 3 shows results of dot hybridization of the Flag. 1 DNA fragment.

Further, a dot hybridization [Biochemistry, 16, 4743–4749 (1977)] was conducted to find that a mouse ADAMTS-1 cDNA labeled with $^{32}$P by a random primed DNA-labeling kit (Boehringer Manmheim GmbH, Germany) was hybridized with the Flag. 1 DNA fragment. The results are shown in FIG. 3. A pCR™2.1 vector as a control was not hybridized with $^{32}$P-labeled mouse ADAMTS-1 cDNA, whereas the mouse ADAMTS-1 cDNA and the Flag. 1 DNA fragment were hybridized with $^{32}$P-labeled mouse ADAMTS-1 cDNA.

The results of the homology search and dot hybridization mean that the Flag. 1 DNA fragment is a part of the human ADAMTS-1.

To obtain a DNA fragment upstream of the Flag. 1 DNA fragment, a Rapid Amplification of cDNA ends (RACE) method using a Marathon cDNA Amplification kit (Clontech Lab. Inc., Palo Alto, Calif., USA) was performed as follows. That is, as back primers for the base sequence of the Flag. 1 DNA fragment, a DNA primer (hereinafter sometimes referred to as a "GSP-1 primer") having the base sequence (i.e., the base sequence of SEQ ID NO: 6: CCTCTTAACT GCACTGTGTC AGT) complementary to the base sequence of the 3'-end region of the Flag. 1 DNA fragment, and a DNA primer (hereinafter sometimes referred to as a "GSP-2 primer") having the base sequence (i.e., the base sequence of SEQ ID NO: 7: CAGGCCCACT CCCAAAGGAA GCTT) complementary to the base sequence of the 5'-end region of the Flag. 1 DNA fragment were chemically synthesized. As forward primers, an AP1 primer and an AP2 primer attached to the above kit were used. The AP1 primer had the base sequence of SEQ ID NO: 8: CCATCCTAAT ACGACT-CACT ATAGGGC, and the AP2 primer had the base sequence of SEQ ID NO: 9: ACTCACTATA GGGCTC-GAGC GGC.

After 5 μl of a human kidney cDNA library (Marathon-Ready cDNA; Clontech Lab. Inc., Palo Alto, Calif., USA), 1 μl of the AP1 primer, 1 μl of 10 μM GSP-1 primer, 1 μl of a Taq polymerase (0.5 unit; Ex Taq polymerase), 1 μl of an anti-Taq polymerase antibody (Taq Start Antibody; Clontech Lab. Inc., Palo Alto, Calif., USA), 5 μl of a PCR buffer having a 10-fold concentration [100 mM Tris-HCl (pH 8.3), 500 mM KCl] (Clontech Lab. Inc., Palo Alto, Calif., USA), and 36 μl of distilled water were mixed, a PCR reaction was performed. The PCR reaction was carried out by repeating a cycle composed of a step at 94° C. for 30 seconds and a step at 68° C. for 4 minutes, 35 times, i.e., 35 cycles. The resulting reaction mixture was diluted to 50-fold with 10 mM Tricine-EDTA buffer (Clontech Lab. Inc., Palo Alto, Calif., USA).

Then, 5 μl of the diluted liquid, 1 μl of the AP2 primer, 1 μl of a 10 μM GSP-2 primer, 1 μl of a Taq polymerase (0.5 unit; Ex Taq polymerase), 1 μl of an anti-Taq polymerase antibody (Taq Start Antibody), 5 μl of a PCR buffer having a 10-fold concentration (Clontech Lab. Inc., Palo Alto, Calif., USA), and 36 μl of distilled water were mixed, and a PCR reaction was then performed. The PCR reaction was carried out by repeating a cycle composed of a step at 94° C. for 30 seconds and a step at 68° C. for 4 minutes 20 times, i.e., 20 cycles.

Figure 4:
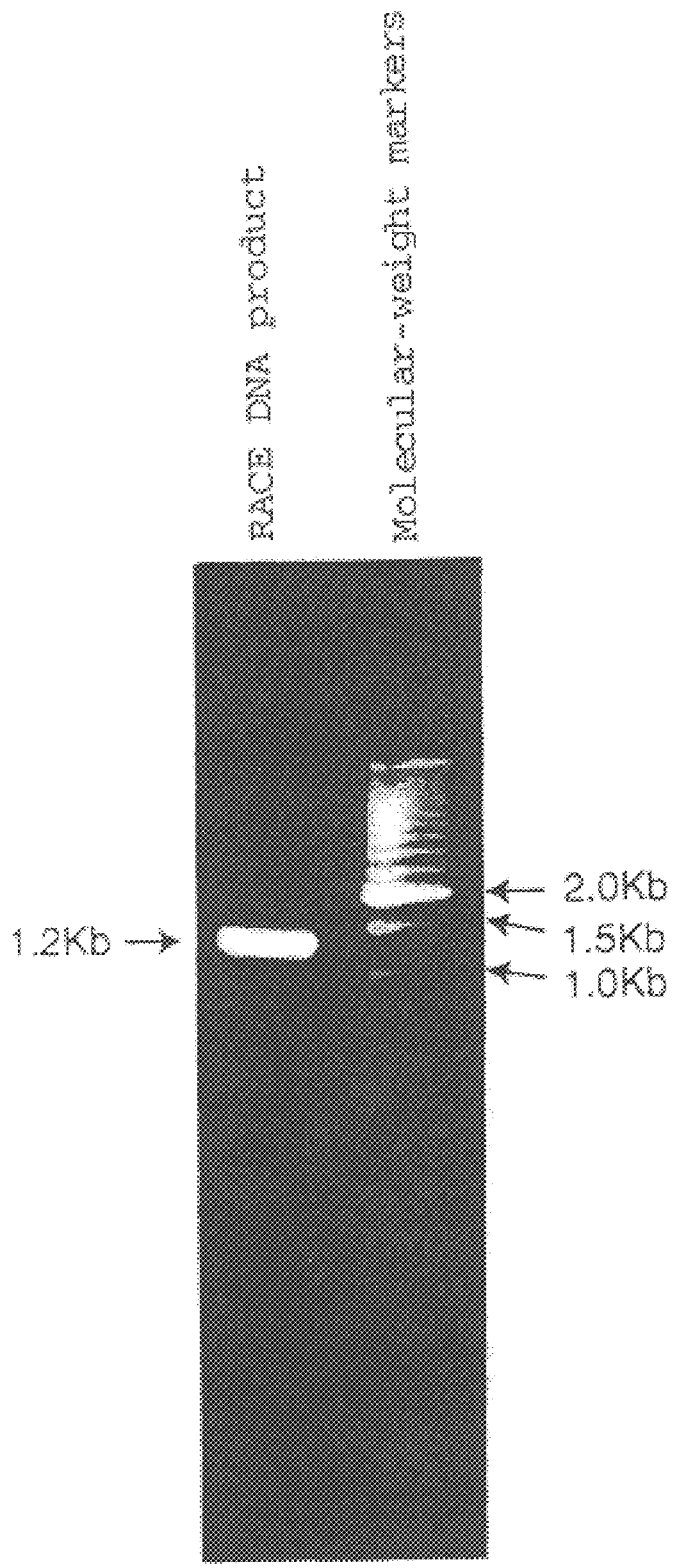
FIG. 4 shows results of an electrophoresis of a Flag. 2 DNA fragment produced by a RACE.

A sample (5 μl) was taken from the resulting reaction mixture, and electrophoresed on 1% agarose gel. As shown in FIG. 4, a single DNA band of about 1.2 Kb was observed. The DNA fragment (hereinafter sometimes referred to as a "Flag. 2 DNA fragment") was cloned in a pCR™ 2.1 vector by a conventional method, and the full-length base sequence of the Flag. 2 DNA fragment determined by a Dye Terminator Cycle Sequencing method (Perkin Elmer Japan, Urayasu, Japan).

Further, the full-length base sequence of the Flag. 1 DNA fragment was determined by the Dye Terminator Cycle Sequencing method (Perkin Elmer Japan, Urayasu, Japan). From the obtained base sequences of the Flag. 1 DNA fragment and the Flag. 2 DNA fragment, the full-length base sequence (2184 bp including a stop codon) is shown in SEQ ID NO: 2 and the amino acid sequence (727 amino acid residues) of the human ADAMTS-1 protein deduced from the above base sequence is shown in SEQ ID NO: 1. The partial base sequence of the Flag. 1 DNA fragment (SEQ ID NO: 14) as shown in FIG. 2 contains some bases not identical to the full-length base sequence of the human ADAMTS-1 cDNA (SEQ ID NO: 2). However, the partial base sequence as shown is FIG. 2 was an interim sequence obtained in the process of determining the base sequence. The base sequence of SEQ ID NO: 2 is a correct base sequence of the human ADAMTS-1 cDNA which has been finally determined.

The human ADAMTS-1 protein is cysteine-rich, and contains many basic amino acids such as lysine and arginine in the C-terminal region, and two N-glycosylation sites (the 307th to 309th amino acids and 524th to 526th amino acids).

The homology between the base sequences of the human ADAMTS-1 gene and the mouse ADAMTS-1 gene is shown in FIGS. 5 to 9, and the homology in the amino acid sequences deduced from the base sequences is shown in FIGS. 10 to 12.

In FIGS. 5 to 9, the symbol "*" means that a base of the human ADAMTS-1 gene is identical to the corresponding base of the mouse ADAMTS-1 gene.

In FIGS. 10 to 12, the symbol "*" means that an amino acid residue of the human ADAMTS-1 protein is identical to the corresponding amino acid residue of the mouse ADAMTS-1 protein. In FIGS. 10 to 12, "MMP domain" means a matrix metalloproteinase domain; the line between the 11th and 12th amino acids indicates the starting site of the matrix metalloproteinase domain; "DI domain" means the disintegrin domain; the line between the 234th and 235th amino acids indicates the starting site of the disintegrin domain; "TSP domain" means the thrombospondin domain; and amino acid sequences in boxes (three occurrences) mean the thrombospondin domain.

The homology in the base sequences between the human ADAMTS-1 and the mouse ADAMTS-1 was 85.5% and that in the amino acid sequences was 90.1%. The results show that ADAMTS-1 is the protein of which, between mouse and human, the sequences have been preserved.

Example 2

Preparation of the Human ADAMTS-1 Fusion Protein in *E. coli*

(1) Construction of an Expression Vector for *E. coli*

To introduce a SmaI site at the 5'-side and a NotI site at the 3'-side into the DNA encoding a partial region downstream of the MMP domain in the full-length human ADAMTS-1 protein, a forward primer (2) having the base sequence of SEQ ID NO: 10: CACCCCGGGA GGAA-GAAGCG ATTTGTGTCC AGCCCCCGTT ATG, and a back primer (2) having the base sequence of SEQ ID NO: 11: GTGGCGGCCG CCCTCTTAAC TGCACTGTGT CAGTGTGCAA AA were chemically synthesized.

After 5 μl of the forward primer (2), 5 μl of the back primer (2), 1 μl of a human kidney cDNA library (Marathon-Ready cDNA; Clontech Lab. Inc., Palo Alto, Calif., USA), 1 μl of a Taq polymerase (0.5 unit; Ex Taq polymerase), 1 μl of an anti-Taq polymerase antibody (Taq Start Antibody; Clontech Lab. Inc., Palo Alto, Calif., USA), 10 μl of a PCR buffer having a 10-fold concentration (Clontech Lab. Inc., Palo Alto, Calif., USA), 8 μl of 2.5 mM 4dNTP (Takarashuzo, Kyoto, Japan), and 69 μl of distilled water were mixed, a PCR reaction was performed. The PCR reaction was carried out by repeating a cycle composed of a step at 94° C. for 1 minute, a step at 55° C. for 45 seconds, and a step at 72° C. for 2 seconds 40 times, i.e., 40 cycles.

Figure 13:
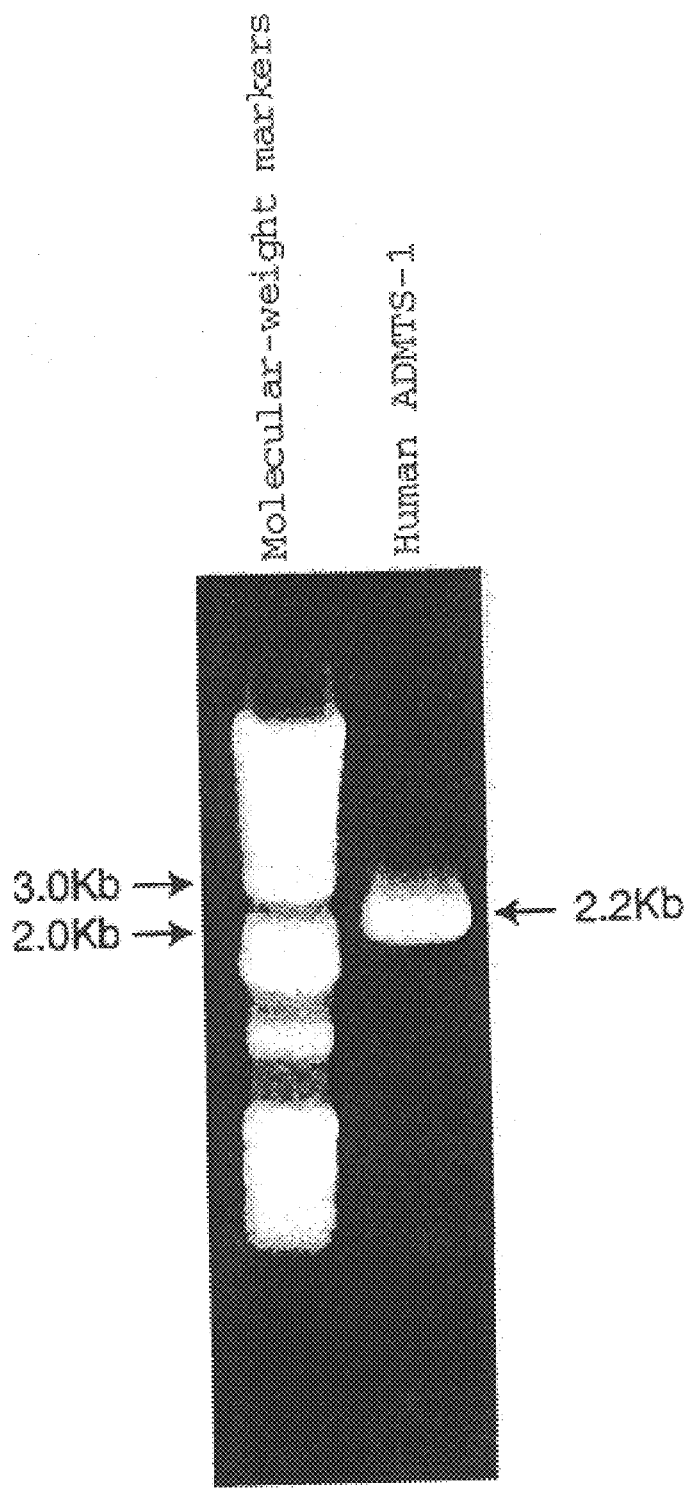
FIG. 13 shows results of an electrophoresis of a full-length cDNA of the human ADAMTS-1 gene of the present invention, the cDNA being produced by a PCR.
Figure 14:
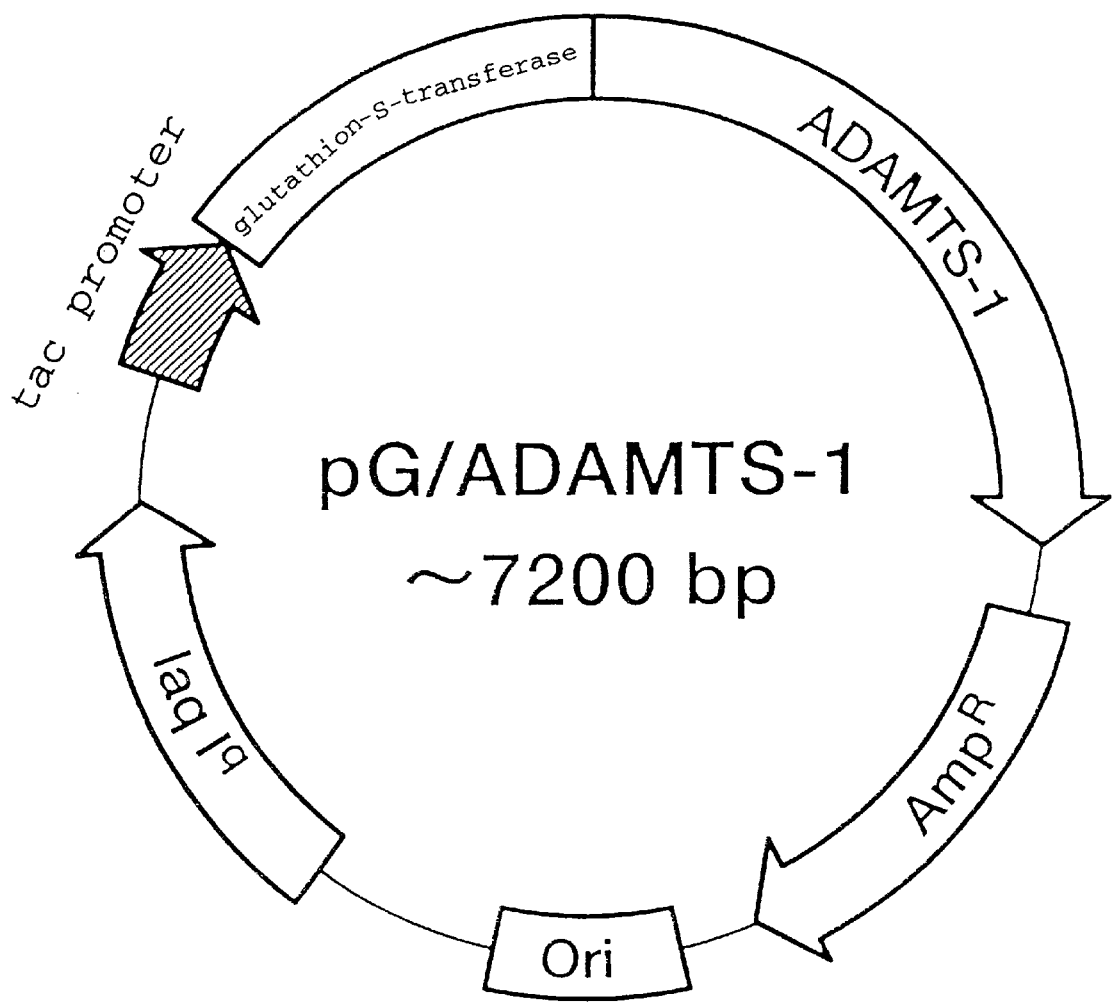
FIG. 14 schematically illustrates a structure of plasmid pG/ADAMTS-1 of the present invention.

A sample (5 μl) was taken from the resulting reaction mixture, and electrophoresed on 1% agarose gel. As shown in FIG. 13, a single DNA band of about 2.2 Kb was obtained. The DNA fragment of about 2.2 Kb was cloned in the pCR™ 2.1 vector by a conventional method, and a large quantity of the plasmids produced [Nucleic Acids Res., 9, 2989–2998 (1981)]. The resulting plasmids prepared on a large scale were treated with restriction enzymes, SmaI (Takarashuzo, Kyoto, Japan) and NotI (Takarashuzo, Kyoto, Japan) to obtain a DNA fragment of about 2.2 Kb. The DNA fragment of about 2.2 Kb was cloned in a SmaI-NotI site of an expression vector for *E. coli* pGEX-5X-1 [Infect Immun., 58, 3909–3913 (1990)] (Pharmacia Biotech, Uppsala, Sweden). The resulting expression plasmid was named pG/ADAMTS-1. The structure of the plasmid pG/ADAMTS-1 is schematically shown in FIG. 14. It is believed that the ADAMTS-1 protein is expressed in the form of a fusion protein (molecular weight=about 96 Kd) with a glutathione-S-transferase (hereinafter sometimes referred to as a "GST") (molecular weight=about 26 Kd). In FIG. 14, "Ori" means a replication origin, "Amp$^R$" means an ampicillin resistance gene, and "laq I$^q$" means a laq repressor.

(2) Expression of the GST-human ADAMTS-1 Fusion Protein in *E. coli*

The plasmid pG/ADAMTS-1 was introduced into an *E. coli* BL-21 strain having a low protease activity (Pharmacia Biotech, Uppsala, Sweden) by a conventional method [Proc. Natl. Acad. Sci. USA, 69, 2110–2114 (1972)]. *E. coli* clones containing the plasmid were isolated as ampicillin resistance strains. Five ampicillin resistance strains (hereinafter referred to as "clone #1" to "clone #5") randomly selected from the strains were used to inoculate 2 ml of 2xYT medium (prepared by dissolving 16 g of trypton, 10 g of yeast extract, and 5 g of NaCl in 1 liter of distilled water; pH 7.2), and cultured overnight at 37° C. Then, a set of two test tubes containing 1800 µl of an LB culture medium containing ampicillin (100 µg/ml) was prepared for each clone. To each test tube, 200 µl of the overnight culture was poured. Then after incubating at 37° C. for 2 hours, 20 µl (final concentration=1.0 mM) of isopropyl-β-D-thiogalactopyranoside (IPTG) (Takarashuzo, Tokyo, Japan), an expression-inducer, was added to one of the two test tubes. Thereafter, the test tubes were incubated at 37° C. for 2 hours. The expression-inducer was not added to the other test tube, which was used as a control.

Microorganisms were harvested by centrifugation (14000 rpm, 1 minute) from 1 ml of the culture, using a microcentrifuging apparatus, then suspended in 100 µl of a phosphate-buffered solution (140 mM NaCl, 2.7 mM KCl, 10 mM Na$_2$HPO$_4$, 1.8 mM KH$_2$PO$_4$, pH 7.2; hereinafter referred to as a PBS) and thereafter dissolved in 100 µl of a 2xsample buffer (0.25M Tris-HCl, 2% SDS, 3% glycerol, 10% β-mercaptoethanol, 0.01% bromophenol blue; pH 6.8). The resulting solution (10 µl) was subjected to an SDS-polyacrylamide gel electrophoresis (hereinafter sometimes referred to as an "SDS-PAGE"), and an expression induction of the desired protein was confirmed by a Coomassie staining method.

Figure 15:
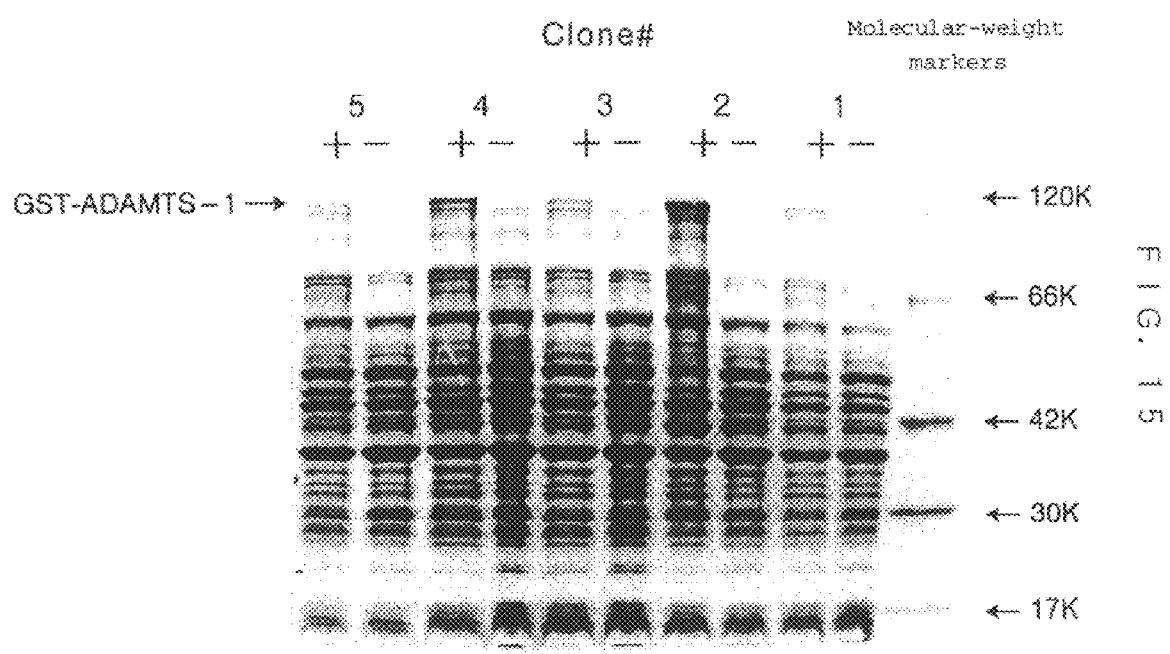
FIG. 15 shows results of an electrophoresis of a transformant transformed by the plasmid pG/ADAMTS-1.

The results are shown in FIG. 15 wherein "+" lanes show the results of the electrophoresis of *E coli* incubated with the expression inducer, IPTG, and "−" lanes show the results of the electrophoresis of *E coli* incubated without the expression inducer, IPTG. In each "+" lane, a protein having a molecular weight of about 100 Kd was observed. This is identical to an expected molecular weight of the GST-human ADAMTS-1 fusion protein, i.e., about 96 Kd. However, such a protein was not observed in the "−" lanes.

Of five clones ("clone #1" to "clone #5"), the clone #2 exhibited the highest expression, and thus was used in the following Examples.

(3) Extraction and Isolation of the GST-human ADAMTS-1 Fusion Protein

After overnight incubation, 1 ml of the culture of the clone #2 was added to 100 ml of a 2xYT culture medium containing 100 µg/ml ampicillin, and incubated at 37° C. When an absorbance at 600 nm reached about 0.5, 1 ml of a 100 mM IPTG was added to the culture, and then incubation was continued for 2 hours.

*E. coli* was harvested by centrifugation (3000 rpm, 30 minutes) from the culture, and then suspended in 8 ml of PBS. To the suspension, 1 ml of 0.5 M EDTA solution and 1 ml of 25 mg/ml lysozyme solution were added, and the whole was allowed to stand in ice for 30 minutes. After 110 µl of Triton X-100 was added, the microorganisms were disrupted on ice by a sonicator (TAITEC, Koshigaya, Japan). The disruption liquid was centrifuged (8000 rpm, 4° C., 10 minutes), then the resulting precipitate suspended in 30 ml of PBS containing 1.0% Triton X-100, and thereafter centrifuged (8000 rpm, 4° C., 10 minutes).

The resulting precipitate was suspended in 2 ml of a 10 mM EDTA solution, and then, 50 ml of a 50 mM Tris-HCl buffer (pH 8.5) containing 8 M urea and 1% mercaptoethanol was added. After a thorough admixing, the mixture was centrifuged (15000 rpm, 4° C., 5 minutes). The resulting supernatant was dialyzed against 5 liters of a 10 mM Tris-HCl buffer (pH 8.5) at 4° C. The dialyzed solution was centrifuged (15000 rpm, 4° C., 5 minutes), and the resulting supernatant then adsorbed to an anion chromatography (Econo-Pac High Q; Bio-Rad Lab., Hercules, Calif., USA). Fractions eluted with 0.2 to 0.4 M NaCl were dialyzed against 3 liters of PBS, and then adsorbed to 1 ml of glutathione Sepharose 4B (Pharmacia Biotech, Uppsala, Sweden) [Nucleic Acids Res., 9, 2989–2998 (1981)].

The glutathione Sepharose 4B was washed with 50 ml of PBS, and then eluted with 8 ml of 10 mM glutathione solution [Nucleic Acids Res., 9, 2989–2998 (1981)]. Fractions exhibiting a high GST activity detected by a GST detecting kit (Pharmacia Biotech, Uppsala, Sweden) were pooled.

Figure 16:
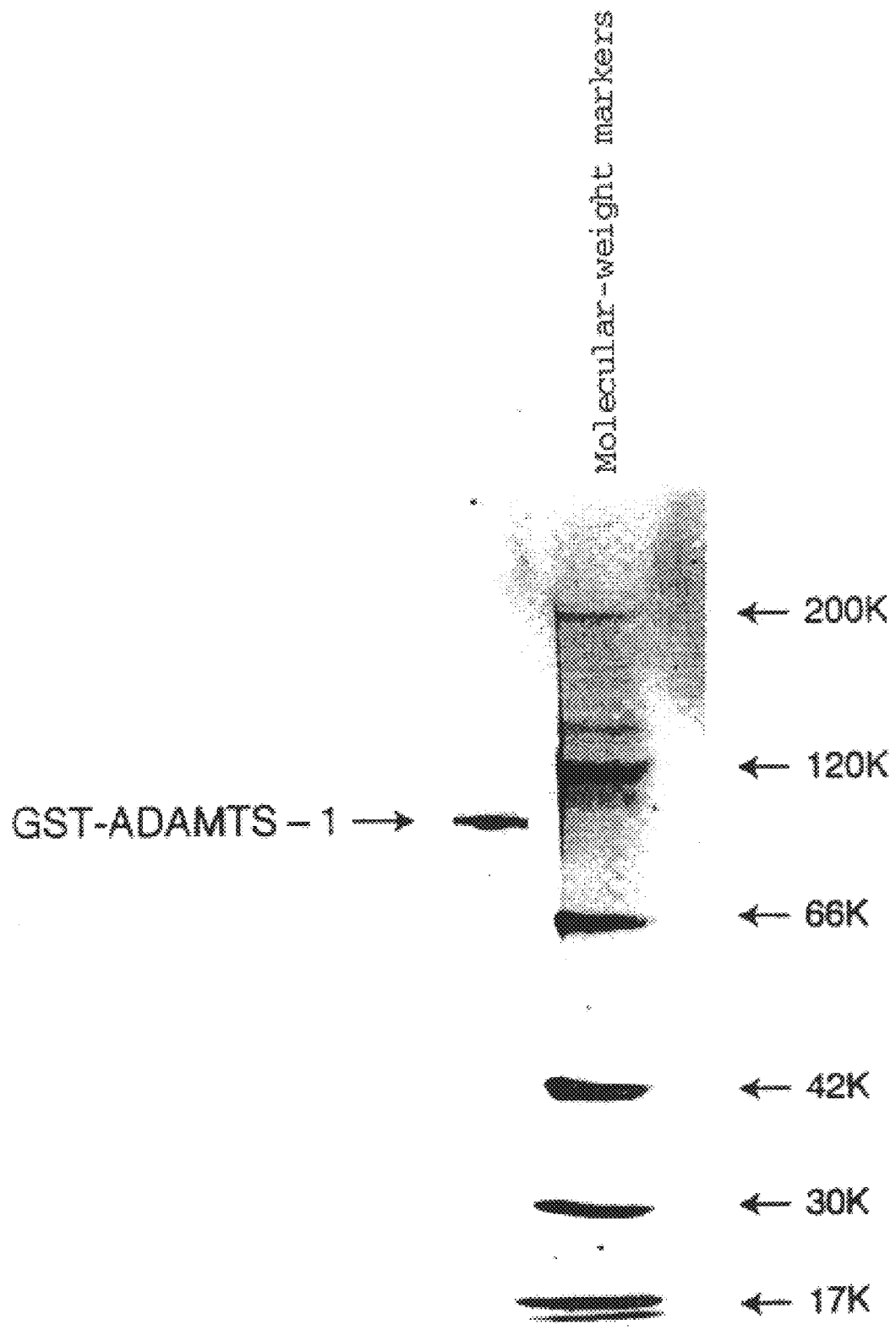
FIG. 16 shows results of an electrophoresis of a GST-human ADAMTS-1 fusion protein.

A part of the fractions was subjected to an SDS-PAGE, and a Coomassie staining was performed. As shown in FIG. 16, a GST-human ADAMTS-1 fusion protein was confirmed from the molecular weight. The desired protein (about 1 µg) was extracted and purified from 100 ml of *E. coli* culture.

The resulting fusion protein contains a site which may be broken with a Factor Xa or the like, between the GST and the human ADAMTS-1 protein, and therefore, the human ADAMTS-1 protein can be obtained by digesting the fusion protein with the proteinase. The human ADAMTS-1 protein may be used as an antigen to prepare an antibody.

Example 3

Examination of Activities of GST-human ADAMTS-1 Fusion Protein on Influencing Hematopoietic Functions To examine the activities of the GST-human ADAMTS-1 fusion protein on influencing hematopoietic functions, a large-scale preparation of the GST-human ADAMTS-1 fusion protein was carried out in accordance with the process disclosed in Example 2 (3), and about 30 µg of the desired protein was obtained from 3 liters of *E. coli* culture.

The functions thought to influence the number of blood cells by a single dosage of the GST-human ADAMTS-1 fusion protein to a tail vein of a mouse were examined, as the activities influencing hematopoietic functions. The examining system can be conducted with a small amount of a protein to be examined, and enables a quick elucidation of a biological activity. In a control test, a GST protein extracted and purified by the process disclosed in Example 2(3) from *E. coli* transformed with a vector pGEX-5X-1 was used.

The GST-human ADAMTS-1 fusion protein (1 µg) was administered to eight C57BL/6N mice (Charlese river Japan, Yokohama, Japan) (male, 7 weeks old) at a tail vein. The numbers of leukocytes, erythrocytes, and platelets were counted 3 hours and 24 hours after the administration. In the control test, the GST protein (1 μg) was administered to eight C57BL/6N mice (Charlese river Japan, Yokohama, Japan) (male, 7 weeks old) at a tail vein. The numbers of leukocytes, erythrocytes, and platelets were counted 3 hours and 24 hours after the administration.

Figure 17:
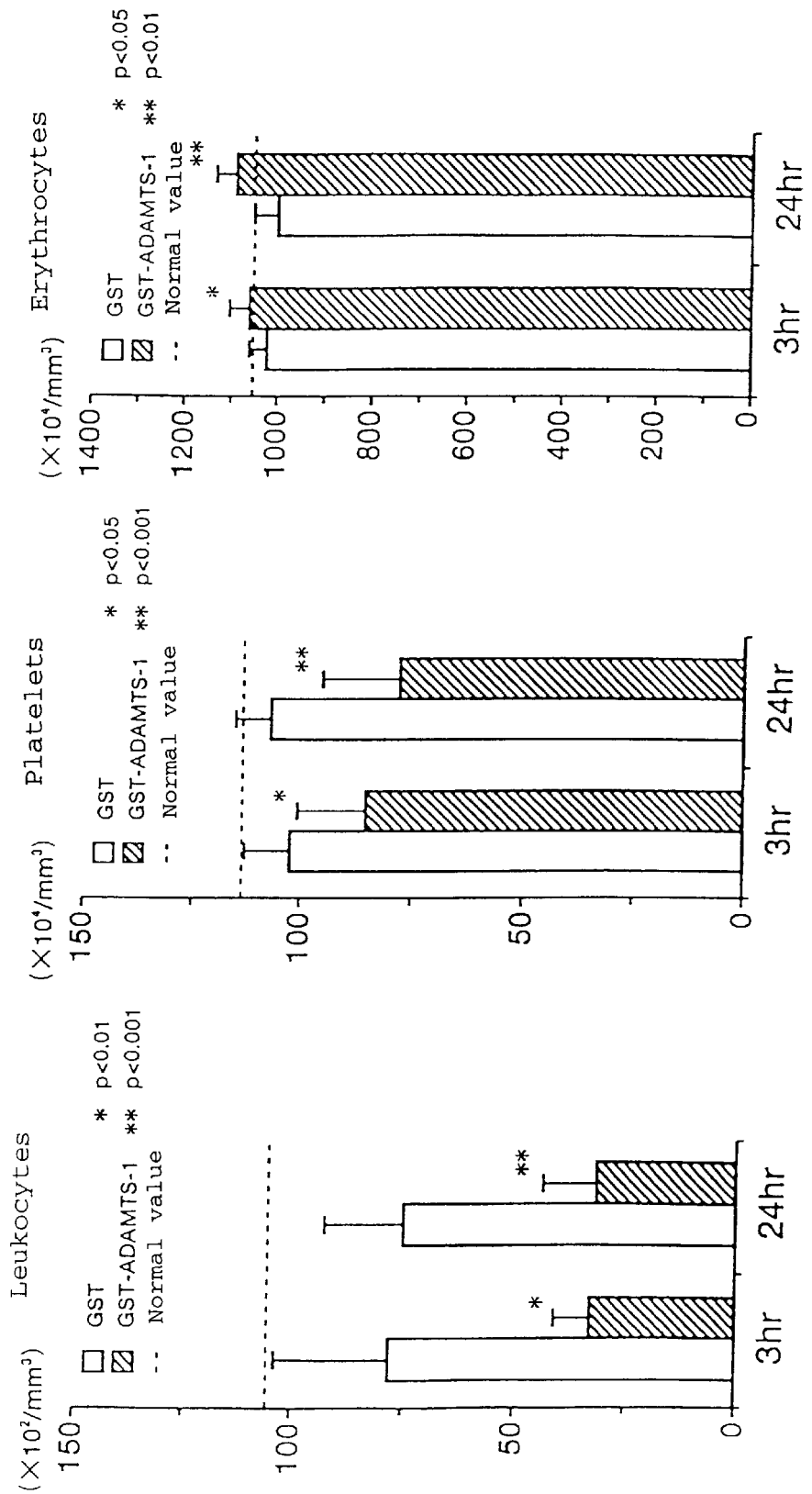
FIG. 17 provides graphs showing effects on the numbers of blood cells when the GST-human ADAMTS-1 fusion protein is intravenously administered to a mouse in a single dosage.

The results are shown in FIG. 17. It is apparent from FIG. 17 that the number of leukocytes and platelets is significantly decreased, and the number of erythrocytes is significantly increased in the mice to which the GST-human ADAMTS-1 fusion protein was administered, in comparison with the control tests.

Industrial Applicability

According to the protein of the present invention, hematopoietic functions can be controlled, for example, the number of leukocytes and platelets can be decreased, and at the same time, the number of erythrocytes can be increased.

As above, the present invention is explained with reference to particular embodiments, but modifications and improvements obvious to those skilled in the art are included in the scope of the present invention.

SEQUENCE LISTING

<160> NUMBER OF SEQ ID NOS: 14

<210> SEQ ID NO 1
<211> LENGTH: 727
<212> TYPE: PRT
<213> ORGANISM: Homo sapiens

<400> SEQUENCE: 1

```
Met Asp Ile Cys Arg Ile Arg Leu Arg Lys Lys Arg Phe Val Ser Ser
1               5                   10                  15

Pro Arg Tyr Val Glu Thr Met Leu Val Ala Asp Gln Ser Met Ala Glu
            20                  25                  30

Phe His Gly Ser Gly Leu Lys His Tyr Leu Leu Thr Leu Phe Ser Val
        35                  40                  45

Ala Ala Arg Leu Tyr Lys His Pro Ser Ile Arg Asn Ser Val Ser Leu
    50                  55                  60

Val Val Val Lys Ile Leu Val Ile His Asp Glu Gln Lys Gly Pro Glu
65                  70                  75                  80

Val Thr Ser Asn Ala Ala Leu Thr Leu Arg Asn Phe Cys Asn Trp Gln
                85                  90                  95

Lys Gln His Asn Pro Pro Ser Asp Arg Asp Ala Glu His Tyr Asp Thr
            100                 105                 110

Ala Ile Leu Phe Thr Arg Gln Asp Leu Cys Gly Ser Gln Thr Cys Asp
        115                 120                 125

Thr Leu Gly Met Ala Asp Val Gly Thr Val Cys Asp Pro Ser Arg Ser
    130                 135                 140

Cys Ser Val Ile Glu Asp Asp Gly Leu Gln Ala Ala Phe Thr Thr Ala
145                 150                 155                 160

His Glu Leu Gly His Val Phe Asn Met Pro His Asp Asp Ala Lys Gln
                165                 170                 175

Cys Ala Ser Leu Asn Gly Val Asn Gln Asp Ser His Met Met Ala Ser
            180                 185                 190

Met Leu Ser Asn Leu Asp His Ser Gln Pro Trp Ser Pro Cys Ser Ala
        195                 200                 205

Tyr Met Ile Thr Ser Phe Leu Asp Asn Gly His Gly Glu Cys Leu Met
    210                 215                 220

Asp Lys Pro Gln Asn Pro Ile Gln Leu Pro Gly Asp Leu Pro Gly Thr
225                 230                 235                 240

Leu Tyr Asp Ala Asn Arg Gln Cys Gln Phe Thr Phe Gly Glu Asp Ser
                245                 250                 255

Lys His Cys Pro Asp Ala Ala Ser Thr Cys Ser Thr Leu Trp Cys Thr
            260                 265                 270

Gly Thr Ser Gly Gly Val Leu Val Cys Gln Thr Lys His Phe Pro Trp
```

```
            275                 280                 285
Ala Asp Gly Thr Ser Cys Gly Glu Gly Lys Trp Cys Ile Asn Gly Lys
    290                 295                 300
Cys Val Asn Lys Thr Asp Arg Lys His Phe Asp Thr Pro Phe His Gly
305                 310                 315                 320
Ser Trp Gly Pro Trp Gly Pro Trp Gly Asp Cys Ser Arg Thr Cys Gly
                325                 330                 335
Gly Gly Val Gln Tyr Thr Met Arg Glu Cys Asp Asn Pro Val Pro Lys
                340                 345                 350
Asn Gly Gly Lys Tyr Cys Glu Gly Lys Arg Val Arg Tyr Arg Ser Cys
                355                 360                 365
Asn Leu Glu Asp Cys Pro Asp Asn Asn Gly Lys Thr Phe Arg Glu Glu
    370                 375                 380
Gln Cys Glu Ala His Asn Glu Phe Ser Lys Ala Ser Phe Gly Ser Gly
385                 390                 395                 400
Pro Ala Val Glu Trp Ile Pro Lys Tyr Ala Gly Val Ser Pro Lys Asp
                405                 410                 415
Arg Cys Lys Leu Ile Cys Gln Ala Lys Gly Ile Gly Tyr Phe Phe Val
                420                 425                 430
Leu Gln Pro Lys Val Val Asp Gly Thr Pro Cys Ser Pro Asp Ser Thr
                435                 440                 445
Ser Val Cys Val Gln Gly Gln Cys Val Lys Ala Gly Cys Asp Arg Ile
450                 455                 460
Ile Asp Ser Lys Lys Lys Phe Asp Lys Cys Gly Val Cys Gly Gly Asn
465                 470                 475                 480
Gly Ser Thr Cys Lys Lys Ile Ser Gly Ser Val Thr Ser Ala Lys Pro
                485                 490                 495
Gly Tyr His Asp Ile Val Thr Ile Pro Thr Gly Ala Thr Asn Ile Glu
                500                 505                 510
Val Lys Gln Arg Asn Gln Arg Gly Ser Arg Asn Asn Gly Ser Phe Leu
                515                 520                 525
Ala Ile Lys Ala Ala Asp Gly Thr Tyr Ile Leu Asn Gly Asp Tyr Thr
    530                 535                 540
Leu Ser Thr Leu Glu Gln Asp Ile Met Tyr Lys Gly Val Val Leu Arg
545                 550                 555                 560
Tyr Ser Gly Ser Ser Ala Ala Leu Glu Arg Ile Arg Ser Phe Ser Pro
                565                 570                 575
Leu Lys Glu Pro Leu Thr Ile Gln Val Leu Thr Val Gly Asn Ala Leu
                580                 585                 590
Arg Pro Lys Ile Lys Tyr Thr Tyr Phe Val Lys Lys Lys Glu Ser
                595                 600                 605
Phe Asn Ala Ile Pro Thr Phe Ser Ala Trp Val Ile Glu Glu Trp Gly
    610                 615                 620
Glu Cys Ser Lys Ser Cys Glu Leu Gly Trp Gln Arg Arg Leu Val Glu
625                 630                 635                 640
Cys Arg Asp Ile Asn Gly Gln Pro Ala Ser Glu Cys Ala Lys Glu Val
                645                 650                 655
Lys Pro Ala Ser Thr Arg Pro Cys Ala Asp His Pro Cys Pro Gln Trp
                660                 665                 670
Gln Leu Gly Glu Trp Ser Ser Cys Ser Lys Thr Cys Gly Lys Gly Tyr
                675                 680                 685
Lys Lys Arg Ser Leu Lys Cys Leu Ser His Asp Gly Gly Val Leu Ser
    690                 695                 700
```

-continued

His Glu Ser Cys Asp Pro Leu Lys Lys Pro Lys His Phe Ile Asp Phe
705                 710                 715                 720

Cys Thr Leu Thr Gln Cys Ser
                725

<210> SEQ ID NO 2
<211> LENGTH: 2184
<212> TYPE: DNA
<213> ORGANISM: Homo sapiens
<220> FEATURE:
<221> NAME/KEY: exon
<222> LOCATION: (1)..(2184)

<400> SEQUENCE: 2

| | | | | | | | | | | | | | | | | |
|---|---|---|---|---|---|---|---|---|---|---|---|---|---|---|---|---|---|
| atg | gat | atc | tgc | aga | att | cgg | ctt | agg | aag | aag | cga | ttt | gtg | tcc | agc | | 48 |
| Met | Asp | Ile | Cys | Arg | Ile | Arg | Leu | Arg | Lys | Lys | Arg | Phe | Val | Ser | Ser | | |
| 1 | | | | 5 | | | | | 10 | | | | | 15 | | | |
| ccc | cgt | tat | gtg | gaa | acc | atg | ctt | gtg | gca | gac | cag | tcg | atg | gca | gaa | | 96 |
| Pro | Arg | Tyr | Val | Glu | Thr | Met | Leu | Val | Ala | Asp | Gln | Ser | Met | Ala | Glu | | |
| | | 20 | | | | | 25 | | | | | 30 | | | | | |
| ttc | cac | ggc | agt | ggt | cta | aag | cat | tac | ctt | ctc | acg | ttg | ttt | tcg | gtg | | 144 |
| Phe | His | Gly | Ser | Gly | Leu | Lys | His | Tyr | Leu | Leu | Thr | Leu | Phe | Ser | Val | | |
| | | | 35 | | | | | 40 | | | | | 45 | | | | |
| gca | gcc | aga | ttg | tac | aaa | cac | ccc | agc | att | cgt | aat | tca | gtt | agc | ctg | | 192 |
| Ala | Ala | Arg | Leu | Tyr | Lys | His | Pro | Ser | Ile | Arg | Asn | Ser | Val | Ser | Leu | | |
| | 50 | | | | | 55 | | | | | 60 | | | | | | |
| gtg | gtg | gtg | aag | atc | ttg | gtc | atc | cac | gat | gaa | cag | aag | ggg | ccg | gaa | | 240 |
| Val | Val | Val | Lys | Ile | Leu | Val | Ile | His | Asp | Glu | Gln | Lys | Gly | Pro | Glu | | |
| 65 | | | | | 70 | | | | | 75 | | | | | 80 | | |
| gtg | acc | tcc | aat | gct | gcc | ctc | act | ctg | cgg | aac | ttt | tgc | aac | tgg | cag | | 288 |
| Val | Thr | Ser | Asn | Ala | Ala | Leu | Thr | Leu | Arg | Asn | Phe | Cys | Asn | Trp | Gln | | |
| | | | | 85 | | | | | 90 | | | | | 95 | | | |
| aag | cag | cac | aac | cca | ccc | agt | gac | cgg | gat | gca | gag | cac | tat | gac | aca | | 336 |
| Lys | Gln | His | Asn | Pro | Pro | Ser | Asp | Arg | Asp | Ala | Glu | His | Tyr | Asp | Thr | | |
| | | | | 100 | | | | | 105 | | | | | 110 | | | |
| gca | att | ctt | ttc | acc | aga | cag | gac | ttg | tgt | ggg | tcc | cag | aca | tgt | gat | | 384 |
| Ala | Ile | Leu | Phe | Thr | Arg | Gln | Asp | Leu | Cys | Gly | Ser | Gln | Thr | Cys | Asp | | |
| | | | 115 | | | | | 120 | | | | | 125 | | | | |
| act | ctt | ggg | atg | gct | gat | gtt | gga | act | gtg | tgt | gat | ccg | agc | aga | agc | | 432 |
| Thr | Leu | Gly | Met | Ala | Asp | Val | Gly | Thr | Val | Cys | Asp | Pro | Ser | Arg | Ser | | |
| | | 130 | | | | | 135 | | | | | 140 | | | | | |
| tgc | tcc | gtc | ata | gaa | gat | gat | ggt | tta | caa | gct | gcc | ttc | acc | aca | gcc | | 480 |
| Cys | Ser | Val | Ile | Glu | Asp | Asp | Gly | Leu | Gln | Ala | Ala | Phe | Thr | Thr | Ala | | |
| 145 | | | | | 150 | | | | | 155 | | | | | 160 | | |
| cat | gaa | tta | ggc | cac | gtg | ttt | aac | atg | cca | cat | gat | gat | gca | aag | cag | | 528 |
| His | Glu | Leu | Gly | His | Val | Phe | Asn | Met | Pro | His | Asp | Asp | Ala | Lys | Gln | | |
| | | | | 165 | | | | | 170 | | | | | 175 | | | |
| tgt | gcc | agc | ctt | aat | ggt | gtg | aac | cag | gat | tcc | cac | atg | atg | gcg | tca | | 576 |
| Cys | Ala | Ser | Leu | Asn | Gly | Val | Asn | Gln | Asp | Ser | His | Met | Met | Ala | Ser | | |
| | | | | 180 | | | | | 185 | | | | | 190 | | | |
| atg | ctt | tcc | aac | ctg | gac | cac | agc | cag | cct | tgg | tct | cct | tgc | agt | gcc | | 624 |
| Met | Leu | Ser | Asn | Leu | Asp | His | Ser | Gln | Pro | Trp | Ser | Pro | Cys | Ser | Ala | | |
| | | | 195 | | | | | 200 | | | | | 205 | | | | |
| tac | atg | att | aca | tca | ttt | ctg | gat | aat | ggt | cat | ggg | gaa | tgt | ttg | atg | | 672 |
| Tyr | Met | Ile | Thr | Ser | Phe | Leu | Asp | Asn | Gly | His | Gly | Glu | Cys | Leu | Met | | |
| | | 210 | | | | | 215 | | | | | 220 | | | | | |
| gac | aag | cct | cag | aat | ccc | ata | cag | ctc | cca | ggc | gat | ctc | cct | ggc | acc | | 720 |
| Asp | Lys | Pro | Gln | Asn | Pro | Ile | Gln | Leu | Pro | Gly | Asp | Leu | Pro | Gly | Thr | | |
| 225 | | | | | 230 | | | | | 235 | | | | | 240 | | |
| ttg | tac | gat | gcc | aac | cgg | cag | tgc | cag | ttt | aca | ttt | ggg | gag | gac | tcc | | 768 |

```
                Leu Tyr Asp Ala Asn Arg Gln Cys Gln Phe Thr Phe Gly Glu Asp Ser
                            245                 250                 255 aaa cac tgc ccc gat gca gcc agc aca tgt agc acc ttg tgg tgt acc              816
Lys His Cys Pro Asp Ala Ala Ser Thr Cys Ser Thr Leu Trp Cys Thr
            260                 265                 270 ggc acc tct ggt ggg gtg ctg gtg tgt caa acc aaa cac ttc ccg tgg              864
Gly Thr Ser Gly Gly Val Leu Val Cys Gln Thr Lys His Phe Pro Trp
            275                 280                 285 gcg gat ggc acc agc tgt gga gaa ggg aaa tgg tgt atc aac ggc aag              912
Ala Asp Gly Thr Ser Cys Gly Glu Gly Lys Trp Cys Ile Asn Gly Lys
290                 295                 300 tgt gtg aac aaa acc gac agg aag cat ttt gat acg cct ttt cat gga              960
Cys Val Asn Lys Thr Asp Arg Lys His Phe Asp Thr Pro Phe His Gly
305                 310                 315                 320 agc tgg gga cca tgg gga ccg tgg gga gac tgt tcg aga acg tgc ggt             1008
Ser Trp Gly Pro Trp Gly Pro Trp Gly Asp Cys Ser Arg Thr Cys Gly
                325                 330                 335 gga gga gtc cag tac acg atg agg gaa tgt gac aac cca gtc cca aag             1056
Gly Gly Val Gln Tyr Thr Met Arg Glu Cys Asp Asn Pro Val Pro Lys
            340                 345                 350 aat gga ggg aag tac tgt gaa ggc aaa cga gtg cgc tac aga tcc tgt             1104
Asn Gly Gly Lys Tyr Cys Glu Gly Lys Arg Val Arg Tyr Arg Ser Cys
            355                 360                 365 aac ctt gag gac tgt cca gac aat aat gga aaa acc ttt aga gag gaa             1152
Asn Leu Glu Asp Cys Pro Asp Asn Asn Gly Lys Thr Phe Arg Glu Glu
370                 375                 380 caa tgt gaa gca cac aac gag ttt tca aaa gct tcc ttt ggg agt ggg             1200
Gln Cys Glu Ala His Asn Glu Phe Ser Lys Ala Ser Phe Gly Ser Gly
385                 390                 395                 400 cct gcg gtg gaa tgg att ccc aag tac gct ggc gtc tca cca aag gac             1248
Pro Ala Val Glu Trp Ile Pro Lys Tyr Ala Gly Val Ser Pro Lys Asp
                405                 410                 415 agg tgc aag ctc atc tgc caa gcc aaa ggc att ggc tac ttc ttc gtt             1296
Arg Cys Lys Leu Ile Cys Gln Ala Lys Gly Ile Gly Tyr Phe Phe Val
            420                 425                 430 ttg cag ccc aag gtt gtt gat ggt act cca tgt agc cca gat tcc acc             1344
Leu Gln Pro Lys Val Val Asp Gly Thr Pro Cys Ser Pro Asp Ser Thr
            435                 440                 445 tct gtc tgt gtg caa gga cag tgt gta aaa gct ggt tgt gat cgc atc             1392
Ser Val Cys Val Gln Gly Gln Cys Val Lys Ala Gly Cys Asp Arg Ile
            450                 455                 460 ata gac tcc aaa aag aag ttt gat aaa tgt ggt gtt tgc ggg gga aat             1440
Ile Asp Ser Lys Lys Lys Phe Asp Lys Cys Gly Val Cys Gly Gly Asn
465                 470                 475                 480 gga tct act tgt aaa aaa ata tca gga tca gtt act agt gca aaa cct             1488
Gly Ser Thr Cys Lys Lys Ile Ser Gly Ser Val Thr Ser Ala Lys Pro
                485                 490                 495 gga tat cat gat atc gtc aca att cca act gga gcc acc aac atc gaa             1536
Gly Tyr His Asp Ile Val Thr Ile Pro Thr Gly Ala Thr Asn Ile Glu
                500                 505                 510 gtg aaa cag cgg aac cag agg gga tcc agg aac aat ggc agc ttt ctt             1584
Val Lys Gln Arg Asn Gln Arg Gly Ser Arg Asn Asn Gly Ser Phe Leu
            515                 520                 525 gcc atc aaa gct gct gat ggc aca tat att ctt aat ggt gac tac act             1632
Ala Ile Lys Ala Ala Asp Gly Thr Tyr Ile Leu Asn Gly Asp Tyr Thr
            530                 535                 540 ttg tcc acc tta gag caa gac att atg tac aaa ggt gtt gtc ttg agg             1680
Leu Ser Thr Leu Glu Gln Asp Ile Met Tyr Lys Gly Val Val Leu Arg
545                 550                 555                 560
```

-continued

```
tac agc ggc tcc tct gcg gca ttg gaa aga att cgc agc ttt agc cct         1728
Tyr Ser Gly Ser Ser Ala Ala Leu Glu Arg Ile Arg Ser Phe Ser Pro
            565                 570                 575 ctc aaa gag ccc ttg acc atc cag gtt ctt act gtg ggc aat gcc ctt         1776
Leu Lys Glu Pro Leu Thr Ile Gln Val Leu Thr Val Gly Asn Ala Leu
        580                 585                 590 cga cct aaa att aaa tac acc tac ttc gta aag aag aag aag gaa tct         1824
Arg Pro Lys Ile Lys Tyr Thr Tyr Phe Val Lys Lys Lys Lys Glu Ser
    595                 600                 605 ttc aat gct atc ccc act ttt tca gca tgg gtc att gaa gag tgg ggc         1872
Phe Asn Ala Ile Pro Thr Phe Ser Ala Trp Val Ile Glu Glu Trp Gly
610                 615                 620 gaa tgt tct aag tca tgt gaa ttg ggt tgg cag aga aga ctg gta gaa         1920
Glu Cys Ser Lys Ser Cys Glu Leu Gly Trp Gln Arg Arg Leu Val Glu
625                 630                 635                 640 tgc cga gac att aat gga cag cct gct tcc gag tgt gca aag gaa gtg         1968
Cys Arg Asp Ile Asn Gly Gln Pro Ala Ser Glu Cys Ala Lys Glu Val
                645                 650                 655 aag cca gcc agc acc aga cct tgt gca gac cat ccc tgc ccc cag tgg         2016
Lys Pro Ala Ser Thr Arg Pro Cys Ala Asp His Pro Cys Pro Gln Trp
            660                 665                 670 cag ctg ggg gag tgg tca tca tgt tct aag acc tgt ggg aag ggt tac         2064
Gln Leu Gly Glu Trp Ser Ser Cys Ser Lys Thr Cys Gly Lys Gly Tyr
        675                 680                 685 aaa aaa aga agc ttg aag tgt ctg tcc cat gat gga ggg gta tta tct         2112
Lys Lys Arg Ser Leu Lys Cys Leu Ser His Asp Gly Gly Val Leu Ser
    690                 695                 700 cat gag agc tgt gat cct tta aag aaa cct aaa cat ttc ata gac ttt         2160
His Glu Ser Cys Asp Pro Leu Lys Lys Pro Lys His Phe Ile Asp Phe
705                 710                 715                 720 tgc aca ctg aca cag tgc agt taa                                          2184
Cys Thr Leu Thr Gln Cys Ser
                725

<210> SEQ ID NO 3
<211> LENGTH: 10
<212> TYPE: PRT
<213> ORGANISM: Mus sp.

<400> SEQUENCE: 3

Arg Thr Cys Gly Gly Gly Val Gln Tyr Thr
1               5                   10

<210> SEQ ID NO 4
<211> LENGTH: 30
<212> TYPE: DNA
<213> ORGANISM: Mus sp.

<400> SEQUENCE: 4
agaacctgtg gtggtggagt tcaatacaca                                           30

<210> SEQ ID NO 5
<211> LENGTH: 32
<212> TYPE: DNA
<213> ORGANISM: Mus sp.

<400> SEQUENCE: 5
cctcttaact gcactgtgtc agtgtgcaaa ag                                        32

<210> SEQ ID NO 6
<211> LENGTH: 23
<212> TYPE: DNA
```

```
<213> ORGANISM: Homo sapiens

<400> SEQUENCE: 6
cctcttaact gcactgtgtc agt                                          23

<210> SEQ ID NO 7
<211> LENGTH: 24
<212> TYPE: DNA
<213> ORGANISM: Homo sapiens

<400> SEQUENCE: 7
caggcccact cccaaaggaa gctt                                         24

<210> SEQ ID NO 8
<211> LENGTH: 27
<212> TYPE: DNA
<213> ORGANISM: Artificial Sequence
<220> FEATURE:
<223> OTHER INFORMATION: AP1 primer

<400> SEQUENCE: 8
ccatcctaat acgactcact atagggc                                      27

<210> SEQ ID NO 9
<211> LENGTH: 23
<212> TYPE: DNA
<213> ORGANISM: Artificial Sequence
<220> FEATURE:
<223> OTHER INFORMATION: AP2 primer

<400> SEQUENCE: 9
actcactata gggctcgagc ggc                                          23

<210> SEQ ID NO 10
<211> LENGTH: 43
<212> TYPE: DNA
<213> ORGANISM: Artificial Sequence
<220> FEATURE:
<223> OTHER INFORMATION: Forward Primer (2)

<400> SEQUENCE: 10
caccccggga ggaagaagcg atttgtgtcc agcccccgtt atg                    43

<210> SEQ ID NO 11
<211> LENGTH: 42
<212> TYPE: DNA
<213> ORGANISM: Artificial Sequence
<220> FEATURE:
<223> OTHER INFORMATION: Back primer (2)

<400> SEQUENCE: 11
gtggcggccg ccctcttaac tgcactgtgt cagtgtgcaa aa                     42

<210> SEQ ID NO 12
<211> LENGTH: 727
<212> TYPE: PRT
<213> ORGANISM: Mus sp.

<400> SEQUENCE: 12

Glu Pro Ser Gly Pro Gly Ser Ile Arg Lys Lys Arg Phe Val Ser Ser
1               5                   10                  15

Pro Arg Tyr Val Glu Thr Met Leu Val Ala Asp Gln Ser Met Ala Asp
                20                  25                  30

Phe His Gly Ser Gly Leu Lys His Tyr Leu Leu Thr Leu Phe Ser Val
```

```
                35                  40                  45
Ala Ala Arg Phe Tyr Lys His Pro Ser Ile Arg Asn Ser Ile Ser Leu
    50                  55                  60

Val Val Val Lys Ile Leu Val Ile Tyr Glu Glu Gln Lys Gly Pro Glu
65                  70                  75                  80

Val Thr Ser Asn Ala Ala Leu Thr Leu Arg Asn Phe Cys Ser Trp Gln
                85                  90                  95

Lys Gln His Asn Ser Pro Ser Asp Arg Asp Pro Glu His Tyr Asp Thr
                100                 105                 110

Ala Ile Leu Phe Thr Arg Gln Asp Leu Cys Gly Ser His Thr Cys Asp
            115                 120                 125

Thr Leu Gly Met Ala Asp Val Gly Thr Val Cys Asp Pro Ser Arg Ser
    130                 135                 140

Cys Ser Val Ile Glu Asp Asp Gly Leu Gln Ala Ala Phe Thr Thr Ala
145                 150                 155                 160

His Glu Leu Gly His Val Phe Asn Met Pro His Asp Asp Ala Lys His
                165                 170                 175

Cys Ala Ser Leu Asn Gly Val Ser Gly Asp Ser His Leu Met Ala Ser
            180                 185                 190

Met Leu Ser Ser Leu Asp His Ser Gln Pro Trp Ser Pro Cys Ser Ala
    195                 200                 205

Tyr Met Val Thr Ser Phe Leu Asp Asn Gly His Gly Glu Cys Leu Met
210                 215                 220

Asp Lys Pro Gln Asn Pro Ile Lys Leu Pro Ser Asp Leu Pro Gly Thr
225                 230                 235                 240

Leu Tyr Asp Ala Asn Arg Gln Cys Gln Phe Thr Phe Gly Glu Glu Ser
                245                 250                 255

Lys His Cys Pro Asp Ala Ala Ser Thr Cys Thr Thr Leu Trp Cys Thr
            260                 265                 270

Gly Thr Ser Gly Gly Leu Leu Val Cys Gln Thr Lys His Phe Pro Trp
    275                 280                 285

Ala Asp Gly Thr Ser Cys Gly Glu Gly Lys Trp Cys Val Ser Gly Lys
290                 295                 300

Cys Val Asn Lys Thr Asp Met Lys His Phe Ala Thr Pro Val His Gly
305                 310                 315                 320

Ser Trp Gly Pro Trp Gly Pro Trp Gly Asp Cys Ser Arg Thr Cys Gly
                325                 330                 335

Gly Gly Val Gln Tyr Thr Met Arg Glu Cys Asp Asn Pro Val Pro Lys
            340                 345                 350

Asn Gly Gly Lys Tyr Cys Glu Gly Lys Arg Val Arg Tyr Arg Ser Cys
    355                 360                 365

Asn Ile Glu Asp Cys Pro Asp Asn Asn Gly Lys Thr Phe Arg Glu Glu
370                 375                 380

Gln Cys Glu Ala His Asn Glu Phe Ser Lys Ala Ser Phe Gly Asn Glu
385                 390                 395                 400

Pro Thr Val Glu Trp Thr Pro Lys Tyr Ala Gly Val Ser Pro Lys Asp
                405                 410                 415

Arg Cys Lys Leu Thr Cys Glu Ala Lys Gly Ile Gly Tyr Phe Phe Val
            420                 425                 430

Leu Gln Pro Lys Val Val Asp Gly Thr Pro Cys Ser Pro Asp Ser Thr
    435                 440                 445

Ser Val Cys Val Gln Gly Gln Cys Val Lys Ala Gly Cys Asp Arg Ile
450                 455                 460
```

-continued

```
Ile Asp Ser Lys Lys Phe Asp Lys Cys Gly Val Cys Gly Gly Asn
465                 470                 475                 480

Gly Ser Thr Cys Lys Lys Met Ser Gly Ile Val Thr Ser Thr Arg Pro
            485                 490                 495

Gly Tyr His Asp Ile Val Thr Ile Pro Ala Gly Ala Thr Asn Ile Glu
            500                 505                 510

Val Lys His Arg Asn Gln Arg Gly Ser Arg Asn Asn Gly Ser Phe Leu
            515                 520                 525

Ala Ile Arg Ala Ala Asp Gly Thr Tyr Ile Leu Asn Gly Asn Phe Thr
            530                 535                 540

Leu Ser Thr Leu Glu Gln Asp Leu Thr Tyr Lys Gly Thr Val Leu Arg
545                 550                 555                 560

Tyr Ser Gly Ser Ser Ala Ala Leu Glu Arg Ile Arg Ser Phe Ser Pro
                565                 570                 575

Leu Lys Glu Pro Leu Thr Ile Gln Val Leu Met Val Gly His Ala Leu
            580                 585                 590

Arg Pro Lys Ile Lys Phe Thr Tyr Phe Met Lys Lys Thr Glu Ser
            595                 600                 605

Phe Asn Ala Ile Pro Thr Phe Ser Glu Trp Val Ile Glu Glu Trp Gly
610                 615                 620

Glu Cys Ser Lys Thr Cys Gly Ser Gly Trp Gln Arg Val Val Gln
625                 630                 635                 640

Cys Arg Asp Ile Asn Gly His Pro Ala Ser Glu Cys Ala Lys Glu Val
                645                 650                 655

Lys Pro Ala Ser Thr Arg Pro Cys Ala Asp Leu Pro Cys Pro His Trp
            660                 665                 670

Gln Val Gly Asp Trp Ser Pro Cys Ser Lys Thr Cys Gly Lys Gly Tyr
            675                 680                 685

Lys Lys Arg Thr Leu Lys Cys Val Ser His Asp Gly Gly Val Leu Ser
690                 695                 700

Asn Glu Ser Cys Asp Pro Leu Lys Pro Lys His Tyr Ile Asp Phe
705                 710                 715                 720

Cys Thr Leu Thr Gln Cys Ser
                725
```

<210> SEQ ID NO 13
<211> LENGTH: 2184
<212> TYPE: DNA
<213> ORGANISM: Mus sp.
<220> FEATURE:
<221> NAME/KEY: exon
<222> LOCATION: (1)..(2184)

<400> SEQUENCE: 13

```
aag cca tca gga cca gga agc ata agg aag aag cga ttt gtg tcc agc    48
Lys Pro Ser Gly Pro Gly Ser Ile Arg Lys Lys Arg Phe Val Ser Ser
1               5                   10                  15 ccc cgt tat gtg gaa acc atg ctc gta gct gac cag tcc atg gcc gac    96
Pro Arg Tyr Val Glu Thr Met Leu Val Ala Asp Gln Ser Met Ala Asp
                20                  25                  30 ttc cac ggc agc ggt cta aag cat tac ctt cta acc ctg ttc tcg gtg   144
Phe His Gly Ser Gly Leu Lys His Tyr Leu Leu Thr Leu Phe Ser Val
            35                  40                  45 gca gcc agg ttt tac aag cat ccc agc att agg aat tca att agc ctg   192
Ala Ala Arg Phe Tyr Lys His Pro Ser Ile Arg Asn Ser Ile Ser Leu
        50                  55                  60
```

-continued

| | | |
|---|---|---|
| gtg gtg gtg aag atc ttg gtc ata tac gag gag cag aag gga cca gaa<br>Val Val Val Lys Ile Leu Val Ile Tyr Glu Glu Gln Lys Gly Pro Glu<br>65                      70                      75                    80 | | 240 |
| gtt acc tcc aat gca gct ctc acc ctt cgg aat ttc tgc agc tgg cag<br>Val Thr Ser Asn Ala Ala Leu Thr Leu Arg Asn Phe Cys Ser Trp Gln<br>                    85                      90                      95 | | 288 |
| aaa caa cac aac agc ccc agt gac cgg gat cca gag cac tat gac act<br>Lys Gln His Asn Ser Pro Ser Asp Arg Asp Pro Glu His Tyr Asp Thr<br>              100                      105                      110 | | 336 |
| gca att ctg ttc acc aga cag gat tta tgt ggc tcc cac acg tgt gac<br>Ala Ile Leu Phe Thr Arg Gln Asp Leu Cys Gly Ser His Thr Cys Asp<br>              115                      120                      125 | | 384 |
| act ctc gga atg gca gat gtt gga acc gta tgt gac ccc agc agg agc<br>Thr Leu Gly Met Ala Asp Val Gly Thr Val Cys Asp Pro Ser Arg Ser<br>130                      135                      140 | | 432 |
| tgc tca gtc ata gaa gat gat ggt ttg caa gct gcc ttc acc aca gcc<br>Cys Ser Val Ile Glu Asp Asp Gly Leu Gln Ala Ala Phe Thr Thr Ala<br>145                      150                      155                    160 | | 480 |
| cat gaa ttg ggc cat gtg ttt aac atg ccg cac gat gat gct aag cac<br>His Glu Leu Gly His Val Phe Asn Met Pro His Asp Asp Ala Lys His<br>                    165                      170                      175 | | 528 |
| tgt gcc agc ttg aat ggt gtg agt ggc gat tct cat ctg atg gcc tcg<br>Cys Ala Ser Leu Asn Gly Val Ser Gly Asp Ser His Leu Met Ala Ser<br>              180                      185                      190 | | 576 |
| atg ctc tcc agc tta gac cat agc cag ccc tgg tca cct tgc agt gcc<br>Met Leu Ser Ser Leu Asp His Ser Gln Pro Trp Ser Pro Cys Ser Ala<br>              195                      200                      205 | | 624 |
| tac atg gtc acg tcc ttc cta gat aat gga cac ggg gaa tgt ttg atg<br>Tyr Met Val Thr Ser Phe Leu Asp Asn Gly His Gly Glu Cys Leu Met<br>        210                      215                      220 | | 672 |
| gac aag ccc cag aat cca atc aag ctc cct tct gat ctt ccc ggt acc<br>Asp Lys Pro Gln Asn Pro Ile Lys Leu Pro Ser Asp Leu Pro Gly Thr<br>225                      230                      235                    240 | | 720 |
| ttg tac gat gcc aac cgc cag tgt cag ttt aca ttc gga gag gaa tcc<br>Leu Tyr Asp Ala Asn Arg Gln Cys Gln Phe Thr Phe Gly Glu Glu Ser<br>                    245                      250                      255 | | 768 |
| aag cac tgc cct gat gca gcc agc aca tgt act acc ctg tgg tgc act<br>Lys His Cys Pro Asp Ala Ala Ser Thr Cys Thr Thr Leu Trp Cys Thr<br>                    260                      265                      270 | | 816 |
| ggc acc tcc ggt ggc tta ctg gtg tgc caa aca aaa cac ttc cct tgg<br>Gly Thr Ser Gly Gly Leu Leu Val Cys Gln Thr Lys His Phe Pro Trp<br>275                      280                      285 | | 864 |
| gca gat ggc acc agc tgt gga gaa ggg aag tgg tgt gtc agt ggc aag<br>Ala Asp Gly Thr Ser Cys Gly Glu Gly Lys Trp Cys Val Ser Gly Lys<br>290                      295                      300 | | 912 |
| tgc gtg aac aag aca gac atg aag cat ttt gct act cct gtt cat gga<br>Cys Val Asn Lys Thr Asp Met Lys His Phe Ala Thr Pro Val His Gly<br>305                      310                      315                    320 | | 960 |
| agc tgg gga cca tgg gga ccg tgg gga gac tgc tca aga acc tgt ggt<br>Ser Trp Gly Pro Trp Gly Pro Trp Gly Asp Cys Ser Arg Thr Cys Gly<br>                    325                      330                      335 | | 1008 |
| ggt gga gtt caa tac aca atg aga gaa tgt gac aac cca gtc cca aag<br>Gly Gly Val Gln Tyr Thr Met Arg Glu Cys Asp Asn Pro Val Pro Lys<br>              340                      345                      350 | | 1056 |
| aac gga ggg aag tac tgt gaa ggc aaa cga gtc cgc tac agg tcc tgt<br>Asn Gly Gly Lys Tyr Cys Glu Gly Lys Arg Val Arg Tyr Arg Ser Cys<br>                    355                      360                      365 | | 1104 |
| aac atc gag gac tgt cca gac aat aac gga aaa acg ttc aga gag gag<br>Asn Ile Glu Asp Cys Pro Asp Asn Asn Gly Lys Thr Phe Arg Glu Glu<br>        370                      375                      380 | | 1152 |

```
cag tgc gag gcg cac aat gag ttt tcc aaa gct tcc ttt ggg aat gag     1200
Gln Cys Glu Ala His Asn Glu Phe Ser Lys Ala Ser Phe Gly Asn Glu
385                 390                 395                 400 ccc act gta gag tgg aca ccc aag tac gcc ggc gtc tcg cca aag gac     1248
Pro Thr Val Glu Trp Thr Pro Lys Tyr Ala Gly Val Ser Pro Lys Asp
            405                 410                 415 agg tgc aag ctc acc tgt gaa gcc aaa ggc att ggc tac ttt ttc gtc     1296
Arg Cys Lys Leu Thr Cys Glu Ala Lys Gly Ile Gly Tyr Phe Phe Val
        420                 425                 430 tta cag ccc aag gtt gta gat ggc act ccc tgt agt cca gac tct acc     1344
Leu Gln Pro Lys Val Val Asp Gly Thr Pro Cys Ser Pro Asp Ser Thr
    435                 440                 445 tct gtc tgt gtg caa ggg cag tgt gtg aaa gct ggc tgt gat cgc atc     1392
Ser Val Cys Val Gln Gly Gln Cys Val Lys Ala Gly Cys Asp Arg Ile
450                 455                 460 ata gac tcc aaa aag aag ttt gat aag tgt ggc gtt tgt gga gga aac     1440
Ile Asp Ser Lys Lys Lys Phe Asp Lys Cys Gly Val Cys Gly Gly Asn
465                 470                 475                 480 ggt tcc aca tgc aag aag atg tca gga ata gtc act agt aca aga cct     1488
Gly Ser Thr Cys Lys Lys Met Ser Gly Ile Val Thr Ser Thr Arg Pro
            485                 490                 495 ggg tat cat gac att gtc aca att cct gct gga gcc acc aac att gaa     1536
Gly Tyr His Asp Ile Val Thr Ile Pro Ala Gly Ala Thr Asn Ile Glu
        500                 505                 510 gtg aaa cat cgg aat caa agg ggg tcc aga aac aat ggc agc ttt ctg     1584
Val Lys His Arg Asn Gln Arg Gly Ser Arg Asn Asn Gly Ser Phe Leu
    515                 520                 525 gct att aga gcc gct gat ggt acc tat att ctg aat gga aac ttc act     1632
Ala Ile Arg Ala Ala Asp Gly Thr Tyr Ile Leu Asn Gly Asn Phe Thr
530                 535                 540 ctg tcc aca cta gag caa gac ctc acc tac aaa ggt act gtc tta agg     1680
Leu Ser Thr Leu Glu Gln Asp Leu Thr Tyr Lys Gly Thr Val Leu Arg
545                 550                 555                 560 tac agt ggt tcc tcg gct gcg ctg gaa aga atc cgc agc ttt agt cca     1728
Tyr Ser Gly Ser Ser Ala Ala Leu Glu Arg Ile Arg Ser Phe Ser Pro
            565                 570                 575 ctc aaa gaa ccc tta acc atc cag gtt ctt atg gta ggc cat gct ctc     1776
Leu Lys Glu Pro Leu Thr Ile Gln Val Leu Met Val Gly His Ala Leu
        580                 585                 590 cga ccc aaa att aaa ttc acc tac ttt atg aag aag aag aca gag tca     1824
Arg Pro Lys Ile Lys Phe Thr Tyr Phe Met Lys Lys Lys Thr Glu Ser
    595                 600                 605 ttc aac gcc att ccc aca ttt tct gag tgg gtg att gaa gag tgg ggg     1872
Phe Asn Ala Ile Pro Thr Phe Ser Glu Trp Val Ile Glu Glu Trp Gly
610                 615                 620 gag tgc tcc aag aca tgc ggc tca ggt tgg cag aga aga gta gtg cag     1920
Glu Cys Ser Lys Thr Cys Gly Ser Gly Trp Gln Arg Arg Val Val Gln
625                 630                 635                 640 tgc aga gac att aac gga cac cct gct tcc gaa tgt gca aag gaa gtg     1968
Cys Arg Asp Ile Asn Gly His Pro Ala Ser Glu Cys Ala Lys Glu Val
            645                 650                 655 aag cca gcc agt acc aga cct tgt gca gac ctt cct tgc cca cac tgg     2016
Lys Pro Ala Ser Thr Arg Pro Cys Ala Asp Leu Pro Cys Pro His Trp
        660                 665                 670 cag gtg ggg gat tgg tca cca tgt tcc aaa act tgc ggg aag ggt tac     2064
Gln Val Gly Asp Trp Ser Pro Cys Ser Lys Thr Cys Gly Lys Gly Tyr
    675                 680                 685 aag aag aga acc ttg aaa tgt gtg tcc cac gat ggg ggc ctg tta tca     2112
Lys Lys Arg Thr Leu Lys Cys Val Ser His Asp Gly Gly Leu Leu Ser
```

```
                  690                 695                 700
aat gag agc tgt gat cct ttg aag aag cca aag cat tac att gac ttt        2160
Asn Glu Ser Cys Asp Pro Leu Lys Lys Pro Lys His Tyr Ile Asp Phe
705                     710                 715                 720 tgc aca ctg aca cag tgc agt taa                                        2184
Cys Thr Leu Thr Gln Cys Ser
                    725

<210> SEQ ID NO 14
<211> LENGTH: 303
<212> TYPE: DNA
<213> ORGANISM: Homo sapiens

<400> SEQUENCE: 14
caagaacctg tggtggtgga gttcattaca cgatgaggga ttgttacaac ccagtcccaa        60
agattggagg gaagtcttgt aaaggcaaac gagtgcccta cagttccttt atcctttagg       120
actgtctaga caattactgg aattcgactt aagagtggcc catcctatgc gccacaccgc       180
gtttcaaaat gtttcctttg ggagttgggc tgcggtggaa ttggttttcc caaggatcgt       240
ggcgtctcac caaaggacag gtgcaagctc atcatgccaa gccaaggat tggctacatt       300 ttc                                                                    303
```

What is claimed is:

1. A pharmaceutical composition comprising a protein containing an amino acid sequence of SEQ ID NO:1, and a pharmaceutically acceptable carrier.

2. A protein comprising an amino acid sequence of SEQ ID NO: 1.

3. A protein consisting essentially of an amino acid sequence of SEQ ID NO:1.

4. A pharmaceutical composition comprising a protein consisting essentially of an amino acid sequence of SEQ ID NO:1 and a pharmaceutically acceptable carrier.

5. A method for reducing leukocytes in vivo, comprising administering to a subject in need of thereof, a pharmaceutical composition as recited in claim 1 or 4 in a therapeutically effective amount.

6. A method for reducing platelets in vivo, comprising administering to a subject in need thereof, a pharmaceutical composition as recited in claim 1 or 4 in a therapeutically effective amount.

7. A method for increasing erythrocytes in vivo, comprising administering to a subject in need thereof, a pharmaceutical composition as recited in claim 1 or 4 in a therapeutically effective amount.

* * * * *

UNITED STATES PATENT AND TRADEMARK OFFICE
CERTIFICATE OF CORRECTION

PATENT NO. : 6,565,858 B2
DATED : May 20, 2003
INVENTOR(S) : Kunitaka Hirose et al.

It is certified that error appears in the above-identified patent and that said Letters Patent is hereby corrected as shown below:

Column 13,
Line 53, delete "*E. coli yeast,*" insert -- *E. coli or yeast,* --

Column 21,
Line 38, delete "of" insert -- or --

Signed and Sealed this

Seventh Day of June, 2005

JON W. DUDAS
*Director of the United States Patent and Trademark Office*